(12) United States Patent
Barnes et al.

(10) Patent No.: US 11,013,456 B2
(45) Date of Patent: *May 25, 2021

(54) SYSTEMS AND METHODS FOR HYPERSPECTRAL MEDICAL IMAGING USING REAL-TIME PROJECTION OF SPECTRAL INFORMATION

(71) Applicant: Spectral Image, Inc., Tampa, FL (US)

(72) Inventors: Michael Barnes, Melbourne Beach, FL (US); Zhihong Pan, Morrisville, NC (US); Sizhong Zhang, Durham, NC (US)

(73) Assignee: Spectral Image, Inc., Tampa, FL (US)

( * ) Notice: Subject to any disclaimer, the term of this patent is extended or adjusted under 35 U.S.C. 154(b) by 483 days.

This patent is subject to a terminal disclaimer.

(21) Appl. No.: 15/887,685

(22) Filed: Feb. 2, 2018

(65) Prior Publication Data

US 2018/0242901 A1 Aug. 30, 2018

Related U.S. Application Data

(63) Continuation of application No. 12/465,150, filed on May 13, 2009, now Pat. No. 9,883,833.

(Continued)

(51) Int. Cl.
*A61B 5/00* (2006.01)
*A61B 5/01* (2006.01)
*A61B 5/0507* (2021.01)

(52) U.S. Cl.
CPC ............ *A61B 5/445* (2013.01); *A61B 5/0059* (2013.01); *A61B 5/015* (2013.01); *A61B 5/0507* (2013.01); *A61B 5/444* (2013.01); *A61B 5/726* (2013.01)

(58) Field of Classification Search
CPC ...... A61B 5/445; A61B 5/0059; A61B 5/0507; A61B 5/015; A61B 5/444; A61B 5/726
See application file for complete search history.

(56) References Cited

U.S. PATENT DOCUMENTS 4,807,622 A 4/1989 Pennypacker et al.
5,772,593 A 6/1998 Hakamata
(Continued)

OTHER PUBLICATIONS

Chan et al., 2007, "Imaging With Terahertz Radiation," Rep. Prog. Phys. 70:1325-1379.

(Continued)

*Primary Examiner* — Joel Lamprecht
(74) *Attorney, Agent, or Firm* — Brett A. Lovejoy; Andrew J. Antczak; Morgan, Lewis & Bockius LLP

(57) ABSTRACT

Under one aspect, a method of displaying medical information about a subject having a plurality of regions includes: resolving light obtained from each region of the plurality of regions into a corresponding spectrum; selecting a portion of each spectrum, the selected portion including medical information about the corresponding region; constructing an image based on the selected portion of each spectrum; and projecting the image onto the subject. Under another aspect, a method of displaying medical information about a subject that has a plurality of regions includes: resolving light obtained from each region of the plurality of regions into a corresponding spectrum; selecting a portion of each spectrum, the selected portion including medical information about the corresponding region; constructing a spectral image based on the selected portion of each spectrum; displaying an image of the plurality of regions; and displaying the spectral image overlying the image of the plurality of regions.

24 Claims, 11 Drawing Sheets

Related U.S. Application Data

(60) Provisional application No. 61/052,934, filed on May 13, 2008.

(56) References Cited

U.S. PATENT DOCUMENTS

| | | | |
|---|---|---|---|
| 5,782,770 | A | 7/1998 | Mooradian et al. |
| 5,969,754 | A | 10/1999 | Zeman |
| 6,118,935 | A | 9/2000 | Samworth |
| 6,236,880 | B1 | 5/2001 | Raylman et al. |
| 6,422,508 | B1 | 7/2002 | Barnes |
| 6,427,022 | B1 | 7/2002 | Craine et al. |
| 6,556,858 | B1 | 4/2003 | Zeman |
| 6,640,130 | B1 | 10/2003 | Freeman et al. |
| 6,640,132 | B1 | 10/2003 | Freeman et al. |
| 6,741,884 | B1 | 5/2004 | Freeman et al. |
| 6,810,279 | B2 | 10/2004 | Mansfield et al. |
| 6,828,558 | B1 | 12/2004 | Arnone et al. |
| 6,937,885 | B1 | 8/2005 | Lewis et al. |
| 6,957,099 | B1 | 10/2005 | Arnone et al. |
| 7,013,172 | B2 | 3/2006 | Mansfield et al. |
| 7,239,909 | B2 | 7/2007 | Zeman |
| D566,283 | S | 4/2008 | Brafford et al. |
| 9,883,833 | B2 * | 2/2018 | Barnes ............... A61B 5/0059 |
| 2003/0123056 | A1 | 7/2003 | Barnes et al. |
| 2004/0010196 | A1 | 1/2004 | Wang et al. |
| 2005/0018987 | A1 | 1/2005 | Ruf et al. |
| 2005/0205667 | A1 | 9/2005 | Rowe |
| 2005/0256745 | A1 | 11/2005 | Dalton |
| 2005/0270528 | A1 | 12/2005 | Geshwind et al. |
| 2006/0028643 | A1 | 2/2006 | Gottlieb et al. |
| 2006/0072109 | A1 | 4/2006 | Bodkin et al. |
| 2006/0082762 | A1 | 4/2006 | Leverette et al. |
| 2006/0122515 | A1 | 6/2006 | Zeman et al. |
| 2006/0153262 | A1 | 7/2006 | Barbieri et al. |
| 2006/0210132 | A1 | 9/2006 | Christiansen et al. |
| 2007/0016079 | A1 | 1/2007 | Freeman et al. |
| 2007/0024946 | A1 | 2/2007 | Panasyuk et al. |
| 2007/0046956 | A1 | 3/2007 | Burlingame |
| 2007/0156038 | A1 | 7/2007 | Zeman et al. |
| 2007/0158569 | A1 | 7/2007 | Zeman |
| 2007/0161906 | A1 | 7/2007 | Zeman et al. |
| 2007/0161907 | A1 | 7/2007 | Goldman et al. |
| 2007/0224694 | A1 | 9/2007 | Puchalski |
| 2007/0249913 | A1 | 10/2007 | Freeman et al. |
| 2008/0004533 | A1 | 1/2008 | Jansen et al. |
| 2008/0045818 | A1 | 2/2008 | Wood |
| 2008/0080755 | A1 | 4/2008 | Payonk et al. |

OTHER PUBLICATIONS

Chen et al., 2005, "Development of a Thermal and Hyperspectral Imaging System for Wound Characterization and Metabolic Correlation," Johns Hopkins APL Technical Digest 26:67-74.

Donner et al., 2006, "A Spectral Shading Model for Human Skin," International Conference on Computer Graphics and Interactive Techniques, ACM SIGGRAPH 2006 Sketches, 1 page.

Khaodhiar et al., 2007, "The Use of Medical Hyperspectral Technology to Evaluate Microcirculatory Changes in Diabetic Foot Ulcers and to Predict Clinical Outcomes," Diabetes Care 30:903-910.

Krishnaswamy, 2005, "Bio Spec: A Biophysically-Based Spectral Model of Light Interaction with Human Skin," Thesis presented to the University of Waterloo, 83 pages.

International Search Report for PCT/US09/02979, dated Jul. 20, 2009, 5 pages.

Mittleman et al., 1999, "Recent Advances in Terahertz Imaging," Appl. Phys. B, 10 pages.

Nakao et al., 1995, "Real-time Multi-spectral Image Processing for Mapping Pigmentation in Human Skin," Proc. Ninth IS&T/SID Color Imaging Conference, IS&T, 7 pages.

Yang et al., 2003, "A CCD Camera-based Hyperspectral Imaging System for Stationary and Airborne Applications," Geocarto International 18(2):71-80.

N.p. (Apr. 12, 2004). "How many types of cancers are there?", Medical News Today. Retrieved from http://www.medicalnewstoday.com/releases/7193.php.

Dawes-Higgs, "Accuracy and reliability of a dynamic biomechanical skin measurement probe for the analysis of stiffness and viscoelasticity", Physiological Measurement, Pub 17, pp. 97-105, Dec. 8, 2003.

U.S. Appl. No. 12/465,150, 2010-0069758, U.S. Pat. No. 9,883,833, Granted, filed May 13, 2009, Mar. 18, 2010, Feb. 6, 2018.

U.S. Appl. No. 12/471,141, 2009-0318815, Abandoned, filed May 22, 2009, Dec. 24, 2009.

U.S. Appl. No. 13/749,576, 2013-0137961, Abandoned, filed Jan. 24, 2013, May 30, 2013.

U.S. Appl. No. 15/197,674, 2017-0150903, Published, filed Jun. 29, 2016, Jun. 1, 2017.

U.S. Appl. No. 12/370,557, 2009-0326383, U.S. Pat. No. 9,117,133, Granted, filed Feb. 12, 2009, Dec. 31, 2009, Aug. 25, 2015.

U.S. Appl. No. 14/800,597, 2016-0080665, Published, filed Jul. 15, 2015, Mar. 17, 2016.

* cited by examiner

SYSTEMS AND METHODS FOR HYPERSPECTRAL MEDICAL IMAGING USING REAL-TIME PROJECTION OF SPECTRAL INFORMATION

CROSS-REFERENCE TO RELATED APPLICATION

This application is a continuation of U.S. patent application Ser. No. 12/465,150, filed May 13, 2009 which claims benefit, under 35 U.S.C. § 119(e), of U.S. Provisional Patent Application No. 61/052,934 filed on May 13, 2008 which is incorporated herein, by reference, in its entirety.

FIELD OF THE APPLICATION

This application generally relates to systems and methods for medical imaging.

BACKGROUND

Affecting more than one million Americans each year, skin cancer is the most prevalent form of cancer, accounting for nearly half of all new cancers reported, and the number is rising. However, according to the American Academy of Dermatology, most forms of skin cancer are almost always curable when found and treated early. For further details, see A. C. Geller et al., "The first 15 years of the American Academy of Dermatology skin cancer screening programs: 1985-1999," Journal of the American Academy of Dermatology 48(1), 34-41 (2003), the entire contents of which are hereby incorporated by reference herein. As the number of patients diagnosed with skin cancer continues to rise year-by-year, early detection and delineation are increasingly useful.

During a conventional examination, dermatologists visually survey the skin for lesions or moles that fit certain pre-defined criteria for a potential malignant condition. If an area is suspect, the doctor will perform a biopsy, sending the tissue to a pathology lab for diagnosis. Though effective, this method of detection is time consuming, invasive, and does not provide an immediate definitive diagnosis of a suspect lesion. It is also vulnerable to false positives that introduce unnecessary biopsy and associated costs. More importantly, early detection is very difficult at best, as developing cancers are not usually visible without close inspection of the skin.

Medical imaging has the potential to assist in the detection and characterization of skin cancers, as well as a wide variety of other conditions.

Hyperspectral medical imaging is useful because, among other things, it allows a physician to obtain information about a patient that is not readily visible to the naked eye. For example, a physician may be able to visually identify the presence of a lesion, but may not be able to visually determine the lesion's actual extent or what type of condition it represents, or for that matter whether the lesion is benign or cancerous. Although the physician may be able to draw tentative conclusions about the lesion based on some general visual indicators such as color and shape, generally a biopsy is needed to conclusively identify the type of lesion. Such a biopsy is invasive, painful, and possibly unnecessary in cases where the lesion turns out to be benign.

In contrast, hyperspectral medical imaging is a powerful tool that significantly extends the physician's ability to identify and characterize medical conditions. "Hyperspectral medical imaging" means utilizing multiple spectral regions to image a subject, e.g., the entire body or a body part of a human or animal, and thus to obtain medical information about that subject. Specifically, each particular region of a subject has a unique spectral signature extending across multiple bands of the electromagnetic spectrum. This spectral signature contains medical, physiological, and compositional information about the corresponding region of the subject. For example, if the subject has a cancerous skin lesion, that lesion may have a different color, density, and/or composition than the subject's normal skin, thus resulting in the lesion having a different spectrum than the normal skin. While these differences may be difficult to visually detect with the naked eye, the differences may become apparent through spectroscopic analysis, thus allowing the lesion (or other medical condition resulting in a measurable spectroscopic feature) to be identified, characterized, and ultimately more readily treated than would be possible using conventional visual inspection and biopsy. Such spectral differences can be presented to a user (such as a physician), for example, by constructing a two-dimensional image of the lesion. See, for example, U.S. Pat. No. 6,937,885, the entire contents of which are incorporated herein by reference. However, such an image can at times make it difficult for the physician to identify exactly what part of the patient's body generated that spectral information.

SUMMARY

Embodiments of the application provide systems and methods of hyperspectral medical imaging.

Under one aspect, a method of displaying medical information about a subject that has a plurality of regions includes: resolving light obtained from each region of the plurality of regions into a corresponding spectrum; selecting a portion of each spectrum, the selected portion including medical information about the corresponding region; constructing an image based on the selected portion of each spectrum; and projecting the image onto the subject.

Some embodiments further include generating the light with a light source. In some embodiments, the light has at least one of a broadband spectrum and a narrowband spectrum. In some embodiments, the light includes at least one of an ultraviolet wavelength, a visible wavelength, an infrared wavelength, and a terahertz wavelength. In some embodiments, resolving the light obtained from each region of the plurality of regions into a corresponding spectrum includes passing the light into a spectrometer. In some embodiments, the spectrometer spatially separates the light into a plurality of component wavelengths, and records an intensity of each component wavelength of the plurality of component wavelengths. In some embodiments, selecting the portion of each spectrum is based on at least one of: a spectral characteristic of a predetermined medical condition, a spectral characteristic of a predetermined physiological feature, and a spectral characteristic of a predetermined chemical. In some embodiments, selecting the portion of each spectrum includes applying a digital filter to a digital signal representing the spectrum. In some embodiments, selecting the portion of each spectrum includes applying at least one of a band-pass filter and a band-block filter to the spectrum. In some embodiments, constructing the image includes assigning the selected portion of each spectrum to at least one of a visible color and an intensity. In some embodiments, projecting the image onto the subject includes projecting the at least one of the visible color and the intensity onto the subject. In some embodiments, the method further includes selecting a different portion of each spectrum, the different selected portion including different medical information about the corresponding region; and constructing a new image based on the different selected portion of each spectrum. Some embodiments include at least one of storing each spectrum and storing the image. In some embodiments, each spectrum is stored in a hyperspectral data cube. In some embodiments, selecting a portion of each spectrum includes at least one of selecting a volume from the hyperspectral data cube and comparing information in the hyperspectral data cube to known spectral information about a medical condition. In some embodiments, the subject is a human. In some embodiments, there is a delay of less than about one minute between resolving light obtained from each region of the plurality of regions and projecting the image onto the subject.

Under another aspect, a system for displaying medical information about a subject that has a plurality of regions includes: a spectrometer for resolving light obtained from each region of the plurality of regions into a corresponding spectrum; logic for selecting a portion of each spectrum, the selected portion including medical information about the corresponding region; logic for constructing an image based on the selected portion of each spectrum; and a projector for projecting the image onto the subject.

Some embodiments further include a light source for irradiating the subject with the light. In some embodiments, the light source generates at least one of a broadband spectrum and a narrowband spectrum. In some embodiments, the light includes at least one of an ultraviolet wavelength, a visible wavelength, an infrared wavelength, and a terahertz wavelength. In some embodiments, the spectrometer includes a diffraction grating for separating the light into a plurality of component wavelengths, and a sensor for recording an intensity of each component wavelength of the plurality of component wavelengths. In some embodiments, the logic selects the portion of each spectrum based on at least one of: a spectral characteristic of a predetermined medical condition; a spectral characteristics of a predetermined physiological feature; and a spectral characteristic of a predetermined chemical. Some embodiments further include a digital filter for digitally selecting the portion of a digital signal representing the spectrum. Some embodiments further include at least one of a band-pass filter and a band-block filter for selecting the portion of each spectrum. In some embodiments, the logic for constructing the image assigns the selected portion of each spectrum to at least one of a visible color and an intensity. In some embodiments, the projector projects the at least one of the visible color and the intensity onto the subject. Some embodiments further include logic for: selecting a different portion of each spectrum, the different selected portion including different medical information about the corresponding region; and constructing a new image based on the different selected portion of each spectrum. Some embodiments further include a storage medium for at least one of storing the image and storing each spectrum. In some embodiments, the storage medium stores each spectrum in a hyperspectral data cube. In some embodiments, selecting a portion of each spectrum includes at least one of selecting a volume from the hyperspectral data cube and comparing information in the hyperspectral data cube to known spectral information about a medical condition. In some embodiments, the subject is a human. In some embodiments, there is a delay of less than about one minute between the spectrometer's resolution of light obtained from each region of the plurality of regions and the projector's projecting the image onto the subject.

Under another aspect, a computer-readable medium storing a computer program executable by a computer for displaying medical information about a subject that has a plurality of regions includes instructions for: obtaining a spectrum corresponding to each region of the plurality of regions; selecting a portion of each spectrum, the selected portion including medical information about the corresponding region; constructing an image based on the selected portion of each spectrum; and providing the image to a projection device for projection onto the subject.

In some embodiments, the computer program further includes instructions for obtaining each spectrum from a spectrometer. In some embodiments, the computer program includes instructions for selecting the portion of each spectrum based on at least one of: a spectral characteristic of a predetermined medical condition, a spectral characteristic of a predetermined physiological feature, and a spectral characteristic of a predetermined chemical. In some embodiments, the computer program includes instructions for selecting the portion of each spectrum by applying a digital filter to a digital signal representing the spectrum.

In some embodiments, the computer program includes instructions for selecting the portion of each spectrum by applying at least one of a band-pass filter and a band-block filter to the spectrum. In some embodiments, the computer program includes instructions for constructing the image by assigning the selected portion of each spectrum to at least one of a visible color and an intensity. In some embodiments, the computer program further includes instructions for: selecting a different portion of each spectrum, the different selected portion including different medical information about the corresponding region; and constructing a new image based on the different selected portion of each spectrum. In some embodiments, the computer program further includes instructions for at least one of storing each spectrum and storing the image. In some embodiments, the computer program further includes instructions for storing each spectrum in a hyperspectral data cube. In some embodiments, the computer program includes instructions for selecting a portion of each spectrum by at least one of selecting a volume from the hyperspectral data cube and comparing information in the hyperspectral data cube to known spectral information about a medical condition.

Under another aspect, a method of displaying medical information about a subject, the subject having a plurality of regions includes: resolving light obtained from each region of the plurality of regions into a corresponding spectrum; selecting a portion of each spectrum, the selected portion including medical information about the corresponding region; constructing a spectral image based on the selected portion of each spectrum; combining the spectral image with other information about the subject to form a composite image; and displaying the composite image.

In some embodiments, displaying the composite image comprises projecting the composite image onto the subject. In some embodiments, displaying the composite image comprises displaying the composite image on a video display. In some embodiments, selecting the portion of each spectrum is based on at least one of: a spectral characteristic of a predetermined medical condition, a spectral characteristic of a predetermined physiological feature, and a spectral characteristic of a predetermined chemical. In some embodiments, the light includes at least one of an ultraviolet wavelength, a visible wavelength, an infrared wavelength, and a terahertz wavelength. In some embodiments, the other information about the subject comprises an image of the subject. In some embodiments, the image of the subject is in at least one of an ultraviolet band, a visible band, an infrared band, and a terahertz band.

Under another aspect, a system for displaying medical information about a subject, the subject having a plurality of regions, includes: a spectrometer for resolving light obtained from each region of the plurality of regions into a corresponding spectrum; logic for selecting a portion of each spectrum, the selected portion including medical information about the corresponding region; logic for constructing a spectral image based on the selected portion of each spectrum; logic for combining the spectral image with other information about the subject to form a composite image; and a display for displaying the composite image.

In some embodiments, the display comprises a projector for projecting the composite image onto the subject. In some embodiments, the display comprises a video display. In some embodiments, the logic selects the portion of each spectrum based on at least one of: a spectral characteristic of a predetermined medical condition, a spectral characteristic of a predetermined physiological feature, and a spectral characteristic of a predetermined chemical. Some embodiments further include a light source for irradiating the subject with the light. In some embodiments, the light includes at least one of an ultraviolet wavelength, a visible wavelength, an infrared wavelength, and a terahertz wavelength. Some embodiments further include an imager for obtaining an image of the subject, and wherein the other information about the subject comprises the image of the subject. In some embodiments, the image of the subject is in at least one of an ultraviolet band, a visible band, an infrared band, and a terahertz band.

Under another aspect, a computer-readable medium stores a computer program executable by a computer for displaying medical information about a subject, the subject having a plurality of regions. The computer program includes instructions for: resolving light obtained from each region of the plurality of regions into a corresponding spectrum; selecting a portion of each spectrum, the selected portion including medical information about the corresponding region; constructing a spectral image based on the selected portion of each spectrum; combining the spectral image with other information about the subject to form a composite image; and displaying the composite image.

In some embodiments, the computer program further comprises instructions for obtaining each spectrum from a spectrometer. In some embodiments, the computer program comprises instructions for displaying the composite image by projecting the composite image onto the subject. In some embodiments, the computer program comprises instructions for displaying the composite image by displaying the composite image on a video display. In some embodiments, the computer program comprises instructions for selecting the portion of each spectrum based on at least one of: a spectral characteristic of a predetermined medical condition, a spectral characteristic of a predetermined physiological feature, and a spectral characteristic of a predetermined chemical. In some embodiments, the other information about the subject comprises an image of the subject at one of an ultraviolet wavelength, a visible wavelength, an infrared wavelength, and a terahertz wavelength.

DETAILED DESCRIPTION

Figure 1:
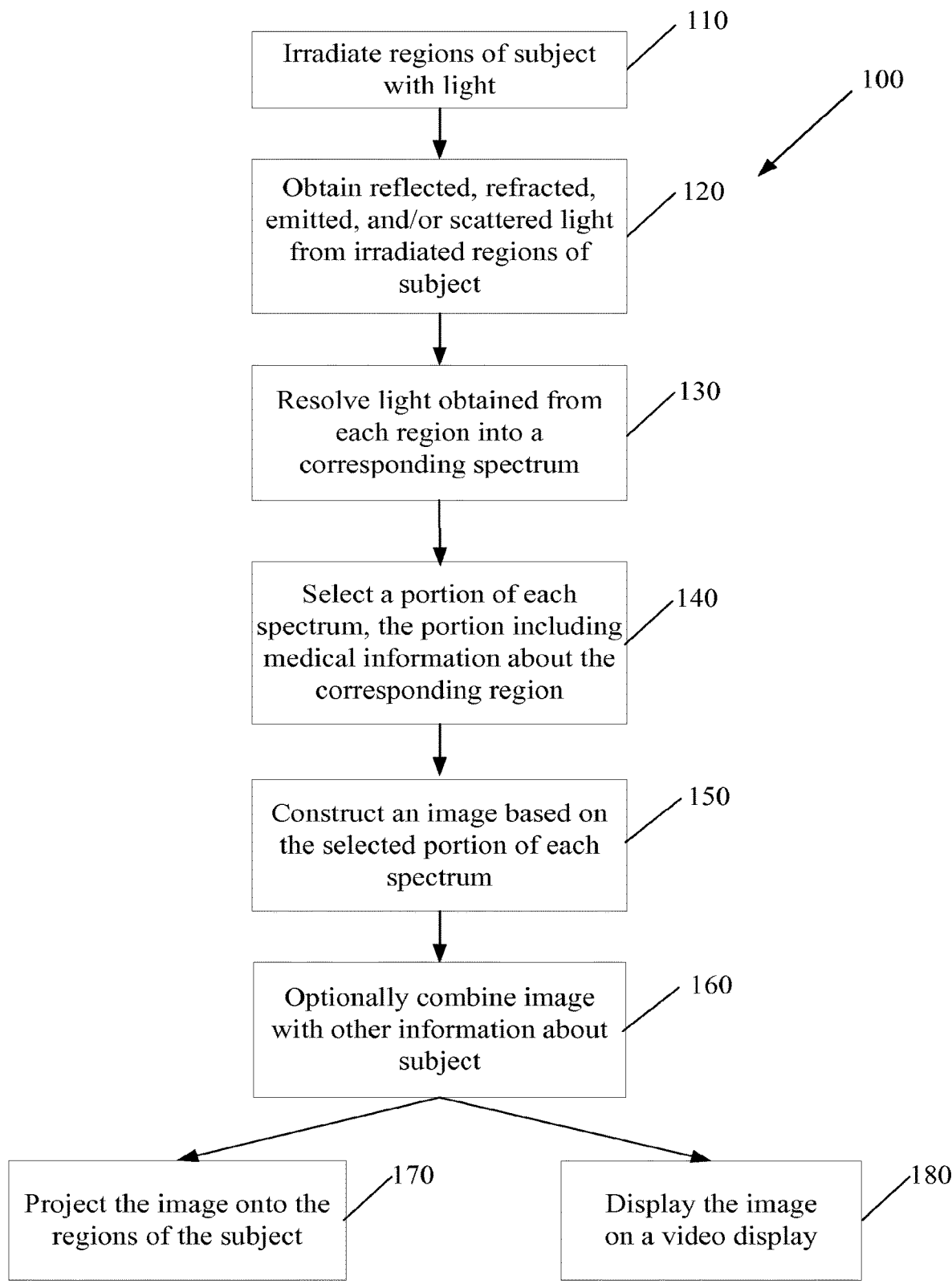
FIG. 1 illustrates a method for hyperspectral medical imaging, according to some embodiments.

Embodiments of the application provide systems and methods for hyperspectral medical imaging.

The present application provides systems and methods that enable a physician to easily examine a subject by projecting spectral information onto the subject and/or by displaying spectral information on a video display. Specifically, the systems and methods include obtaining hyperspectral information from the subject, for example, by irradiating a region of the subject with a light source, and collecting and spectrally analyzing the light from the subject. The systems and methods include creating an image that maps the spectrally analyzed light onto visible cues (such as false colors and/or intensity distributions) that represent spectral features that include medical information about the subject. In some embodiments, the systems and methods include projecting those visible cues back onto the region of the subject in "real time" (that is, preferably with an imperceptible delay between irradiation and projection). This allows the physician to concurrently or contemporaneously inspect both the subject and the spectral information about the subject, which is represented by the visible cues that are projected back upon the subject. The visible cues are projected directly onto the regions of the subject having the spectral features upon which those visible cues are based and/or displayed on a video display.

Optionally, the projected and/or displayed image includes not only the visible cues representing spectral information about the subject, but also other types of information about the subject. For example, a conventional visible-light image of the subject (e.g., as recorded by a conventional video camera) can be obtained, and the spectral information overlaid on that conventional image in order to aid in correlation between the spectral features and the regions that generated those features. Or, for example, information can be obtained from multiple types of sensors (e.g., LIDAR, color, thermal) and that information combined with the hyperspectral image, thus simultaneously providing different, and potentially, complementary types of information about the subject.

In some embodiments, the steps of obtaining light from the subject, processing that light to obtain an image, and projecting that image onto the subject and/or displaying the image are performed with only a brief delay between steps, so that the physician can view the images projected onto the subject while he/she is examining the subject. For example, the delay between obtaining the light and projecting the image may be less than about 1 ms, less than about 10 ms, less than about 100 ms, less than about 1 second, less than about 10 seconds, or less than about 1 minute. Regardless of any delay between obtaining the light and projecting and/or displaying the image, in some embodiments the obtained light and the projected/displayed light are separated from each other, either spectrally or temporally, in order to inhibit feedback of the projected light into the system. To "spectrally" separate the obtained and projected light, the projected light can be limited to a small spectral range that is not used for spectral analysis; to "temporally" separate the obtained and projected light, the light is first obtained from the subject, and the image then projected onto the subject without overlapping between these two steps.

First, a brief overview of methods of hyperspectral medical imaging will be provided. Then, systems for hyperspectral medical imaging will be described in detail. The described methods and systems are merely exemplary, and not limiting.

FIG. 1 provides an overview of a method 100 of hyperspectral medical imaging, according to some embodiments.

First, a plurality of regions of the subject are irradiated with light (110). Collectively, the regions of the subject can include, for example, a portion of one of the subject's body parts, an entire body part, multiple body parts, or the entire subject. However, each individual region may be quite small, e.g., less than 10 centimeters in area, or less than 1 centimeter in area, or less than 100 millimeters in area, or less than 10 millimeters in area, or less than 1 millimeter in area, or less than 100 microns in area. Usefully, each individual region is sufficiently small to allow resolution of the medical feature of interest, that is, so that a specified region containing the medical feature can be distinguished from other regions that do not contain the feature. Different options for the source and spectral content of the light are described in greater detail below.

Next, light is obtained from the regions of the subject (120). Depending on the interactions between the regions of the subject and the spectrum of light with which they are irradiated, the light may be reflected, refracted, absorbed, and/or scattered from the regions of the subject. In some embodiments, one or more regions of the subject may even emit light, e.g., fluoresce or photoluminesce in response to irradiation with the light. A lens, mirror, or other suitable optical component can be used to obtain the light from the regions of the subject, as described in greater detail below.

The light obtained from each region is then resolved into a corresponding spectrum (130). For example, the light obtained from each region can be passed into a spectrometer. The spectrometer includes a diffraction grating or other dispersive optical component that generates a spatial separation between the light's component wavelengths. This spatial separation allows the relative intensities of the component wavelengths in the spectrum to be obtained and recorded, e.g., using a detector such as a charge-coupled device (CCD) or other appropriate sensor that generates a digital signal representing the spectrum. The digital signal corresponding to each region can be stored, e.g., on readable media or in random access memory. Examples of suitable detectors include, but are not limited to, Si CCD, InGaAs, and HgCdTe. Suitable spectral ranges in some embodiments is 0.3 microns to 1 micron, 0.4 micron to 1 micron, 1 micron to 1.7 microns, or 1.3 microns to 2.5 microns. In some embodiments the detector contains between 320 and 1600 spatial pixels. In other embodiments, the detector has more or less spatial pixels. In some embodiments, the detector has a field of view across track that is between 14 degrees and 18.4 degrees. In some embodiments the detector samples at a rate of between 3 nm and 10 nm. In some embodiments, the detector samples between 64 and 256 spectral bands. Of course, it is expected over time that improved detectors will be devised and any such improved detector may be used in accordance with the systems and methods of the present invention.

A portion of each spectrum is then selected (140). The selected portion includes medical information about the corresponding region. For example, selecting the portion of each spectrum may include filtering the spectrum based on the spectral characteristics of a predetermined medical condition, predetermined physiological feature, or predetermined chemical (e.g., pharmaceutical compound). The selected portion of each spectrum thus includes medical information about that region. In embodiments in which digital signal representing the spectrum is generated, one or more portions of that digital signal can be modified (e.g., amplified or deleted) in order to select the desired portion. Exemplary algorithms for selecting portions of spectra are described in greater detail below.

An image based on the selected portion of each spectrum is then constructed (150). The image includes information about the relative intensities of selected wavelengths within the various regions of the subject, and thus includes medical information about those regions. The image can represent the spectral information in a variety of ways. For example, the image may include a two-dimensional map that represents the intensity of one or more selected wavelengths within each region of the subject. Such image can be monochromatic, with the intensity of the map at a given region based on the intensity of the selected wavelengths (e.g., image intensity directly proportional to light intensity at the selected wavelengths). Alternately, the image can be colorful, with the color of the map at a given region based on the intensity of the selected wavelengths, or indices deducted from the selected wavelengths (more below). Although the image may represent information from one or more non-visible regions of the electromagnetic spectrum (e.g., infrared), the image itself is typically at least partially in the visible range, so that it can be viewed by a physician or other interested party. Examples of images are provided below.

The image is then optionally combined or "fused" with other information about the subject (160). For example, the image can be overlaid on a conventional visible-light image of the subject, and/or can be combined with the output of other types of sensors. In some embodiments, spectral data from one source, such as a hyperspectral image, is scaled to a grey scale or color whereas as spectral data from another completely independent source (e.g., x-rays, molecular resonance imaging, nuclear magnetic resonance, a dynamic biomechanical skin measurement probe) that is measured concurrently with the spectral image is topographically scaled to form a topographical or contour map. In such embodiments, the topographical or contour map can be colored based on the grey scale or color scaled hyperspectral image data. Of course, the reverse is also true, where the hyperspectral image data is converted to a topographical or contour map and the spectral data from the independent spectral source is normalized to a color scale or a grey scale which is then used to color the topographical or contour map. Usefully, such a combined map can emphasize skin abnormalities that may not be apparent from any one source of spectral data. For instance, if one spectral source flags a particular region of the screen with a "red" result where red represents one end of the dynamic range of the sensor and another independent spectral source assigns a dense peak to this same region, where the peak represents the limits of the dynamic range of this independent spectral source, the combined image from the two spectral sources will show a peak that is colored red. This can aid a physician in pinpointing a region of interest. Two or more independent spectral sources can be used. In some embodiments, two or more, three or more, four or more, five or more spectral sources are combined into a single image. In some embodiments, some spectral sources are displayed in complementary (orthogonal) ways such as the example of a topographical map that is colored based on the results of a different spectral source. In some embodiments, some spectral sources are combined using statistical techniques such as principal component analysis. In some embodiments, some spectral sources are combined in an additive manner. For example, in some embodiments, the corresponding pixel values of two spectral images taken using different spectral sources are simply added together to form a fused image. Any such pixel by pixel based combination of spectral images is within the scope of the present invention. In some embodiments, such spectral images taken using different spectroscopic means are taken concurrently so that the register of such images with respect to the skin of the patient and to the respective spectral images is all known. In some embodiments, such spectral images are taken sequentially but near in time with the assurance that the subject has not moved during the sequential measurements so that the images are readily combined. In some embodiments, a skin registry technique is used that allows for the images from different spectral sources to be taken at different times and then merged together. For instance, a transparent grid can be fastened to the subject's skin and the grid marks in each of the resultant spectra taken of the subject can be used to align different images together. Concurrently using different types of sensors provides a powerful way of obtaining rich information about the subject. Specific types of sensors and/or data fusion methods may be used to analyze different types of targets. For example, in remote sensing analysis, a sensor specific for submerged aquatic vegetation (SAV) has been employed. Furthermore, normalized difference vegetation index (NDVI) is also developed for better representation. Similarly, in medical imaging, specific sensors may be used to detect changes in specific types of tissues, substances, or organs. Indices similar to NDVI can also be developed to normalize certain types of tissues, substances, or organs, either to enhance their presence or to reduce unnecessary background noise.

The rich information obtained by multi-sensor analyses may be integrated by data fusion methods in order to enhance image qualify or to add additional information that is missing in the individual images. Image fusion methods can be broadly classified into two categories: 1) visual display transforms which involves the color composition of three bands of imagery displayed in red-green-blue (RGB) or other color transformations such as intensity-hue-saturation (IHS); and 2) statistical or numerical transforms based on channel statistics and include, for example, principal component analysis (PCA). Image fusion methods that may be applied to the instant invention include, but are not limited to, band overlay, high-pass filtering (HPF), intensity-hue-saturation (IHS) transformation, discrete wavelet transform (DWT), and principal component analysis (PCA).

Band Overlay.

The band overlay (band substitution) is the simplest image fusion technique. The major advantage of this technique is that there is no changes to the radiometric qualities of the data since there is no radiometric enhancement of the data. In some embodiments, the technique is used when the two sources are highly correlated. Panchromatic sharpening involves the substitution of the panchromatic band for the multi-spectral band covering the same region as the panchromatic band. The generation of color composite images is limited to the display of only three bands corresponding to the color guns of the display device (red-green-blue). As the panchromatic band has a spectral range covering both the green and red channels (PAN 0.50-0.75 mm; green 0.52-0.59 mm; red 0.62-0.68 mm), the panchromatic band can be used as a substitute for either of those bands.

High-Pass Filtering Method (HPF).

The HPF fusion method is a specific application of arithmetic techniques used to fuse imagery, which involves use of arithmetic operations such as addition, subtraction, multiplication and division. HPF is an arithmetic technique that applies a spatial enhancement filter to the high-resolution image before the two data sets are merged together on a pixel-by-pixel basis. The HPF fusion combines both spatial and spectral information using the band-addition approach. It has been found that when compared to the IHS and PCA, the HPF method exhibits less distortion in the spectral characteristics of the data; and distortions are minimal and difficult to detect. This conclusion is based on statistical, visual and graphical analysis of the spectral characteristics of the data.

Intensity-Hue-Saturation (IHS).

IHS transformation is one of the most widely used methods for merging complementary, multi-sensor data sets. The IHS transform provides an effective alternative to describing colors by the red-green-blue display coordinate system. The possible range of digital numbers (DNs) for each color component is 0 to 255 for 8-bit data. Each pixel is represented by a three-dimensional coordinate position within the color cube. Pixels having equal components of red, green and blue lie on the grey line, a line from the cube to the opposite corner. The IHS transform is defined by three separate and orthogonal attributes, namely intensity, hue, and saturation. Intensity represents the total energy or brightness in an image and defines the vertical axis of the cylinder. Hue is the dominant or average wavelength of the color inputs and defines the circumferential angle of the cylinder. It ranges from blue (0/360°) through green, yellow, red, purple, and then back to blue (360/0°). Saturation is the purity of a color or the amount of white light in the image and defines the radius of the cylinder. Of all methods to merge multi-spectral data, the IHS method distorts spectral characteristics the most and should be used with caution if detailed radiometric analysis is to be performed. Although IRS 1C LISS III acquires data in four bands, only three bands are used for the study neglecting the fourth due to the poor spatial resolution. IHS transform is more successful in panchromatic sharpening with true color composites than when the color composites include near or mid-infrared bands.

Principal Component Analysis (PCA).

The PCA is a commonly used tool for image enhancement and the data compression. The original inter-correlated data are mathematically transformed into new, uncorrelated images called components or axes. The procedure involves a linear transformation so that the original brightness values are re-projected onto a new set of orthogonal axes. PCA is a relevant method for merging remotely sensed imagery because of its ability to reduce the dimensionality of the original data from n to 2 or 3 transformed principal component images, which contains the majority of the information from the original spectroscopic data sources. For example, PCA can be used to merge several bands of multispectral data with one high spatial resolution band. Image fusion can be done in two ways using the PCA. The first method is very similar to IHS transformation. The second method involves a forward transformation that is performed on all image channels from the different sensors combined to form one single image file.

Discrete Wavelet Transform (DWT).

The DWT method involves wavelet decomposition where wavelet transformation converts the images into different resolutions. Wavelet representation has both the spatial and frequency components. Exemplary approaches for wavelet decomposition includes the Mallat algorithm which can use wavelet function such as the Daubechies functions (db1, db2, . . . ) and the à Trous algorithm which merges dyadic wavelet and non_dyadic data in a simple and efficient procedure. There are two approaches for image fusion based on wavelet decomposition: the substitution method and the additive method. In the substitution method, after the wavelet coefficients of multispectral and panchromatic images are obtained, some wavelet coefficients of multispectral image are substituted by wavelet coefficients of panchromatic image followed by an inverse wavelet transform. In the additive method, wavelet planes of the panchromatic image may be produced and added to the red, green, and blue bands directly or to the intensity component which is extracted from the red, green, and blue bands. In some embodiments, a transformation step may be used to convert the HIS component (with a new intensity) into new R,G,B data.

More detailed description of the exemplary imagery fusion methods can be found in, for example, Harris et al., 1990, "IHS transform for the integration of radar imagery with other remotely sensed data," Photogrammetric Engineering and Remote Sensing, 56(12): 1631-1641; Phol and van Genderen, 1998, "Multisensor image fusion in remote sensing: concepts, methods and applications," International Journal of Remote Sensing, 19(5): 823-854; Chavez et al., 1991, "Comparison of three different methods to merge multi-resolution and multi-sectoral data: Landsat™ and SPOT Panchromatic," Photogrammetric Engineering and Remote Sensing, 57(3): 295-303; Pellemans et al., 1993, "Merging multispectral and panchromatic SPOT images with respect to radiometric properties of the sensor," Photogrammetric Engineering and Remote Sensing, 59(1): 81-87; Nunez et al., 1999, "Multiresolution based image fusion with additive wavelet decomposition," IEEE Transactions on Geoscience and Remote Sensing, 37(3): 1204-1211; Steinnocher, 1997, "Applications of adaptive filters for multisensoral image fusion," Proceedings of the International Geoscience and Remote Sensing Symposium (IGARASS '97), Singapore, August 1997, 910-912; and Chavez and Kwarteng, 1989, "Extracting spectral contrast in Landsat Thematic Mapper image data using selective principal component analysis," Photogrammetric Engineering and Remote Sensing, 55(3): 339-348, each of which is hereby incorporated by reference herein in its entirety.

Figure 7A:
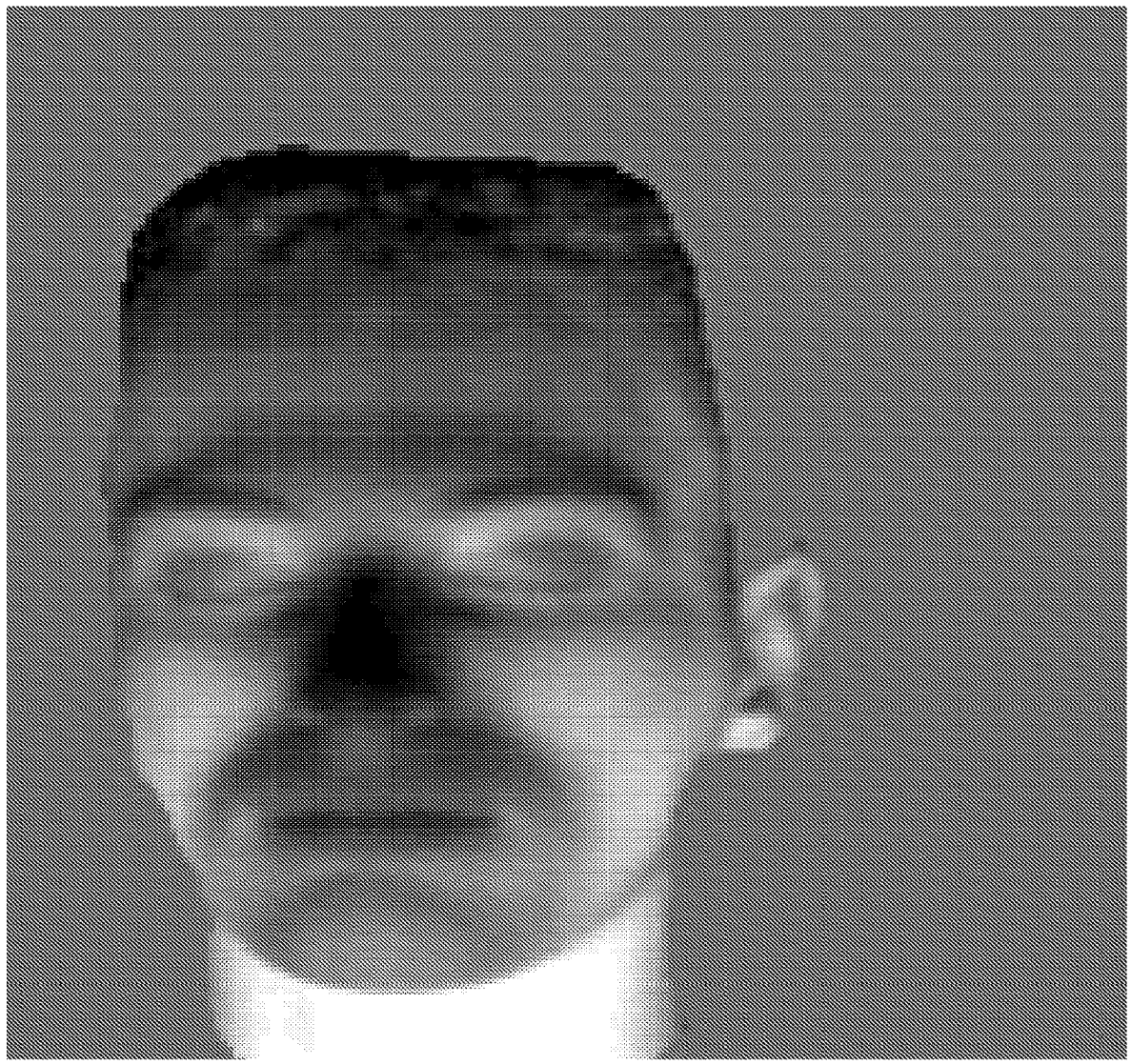
FIGS. 7A-7C are exemplary images from different spectral bands that contain different medical information about a subject.
Figure 7B:
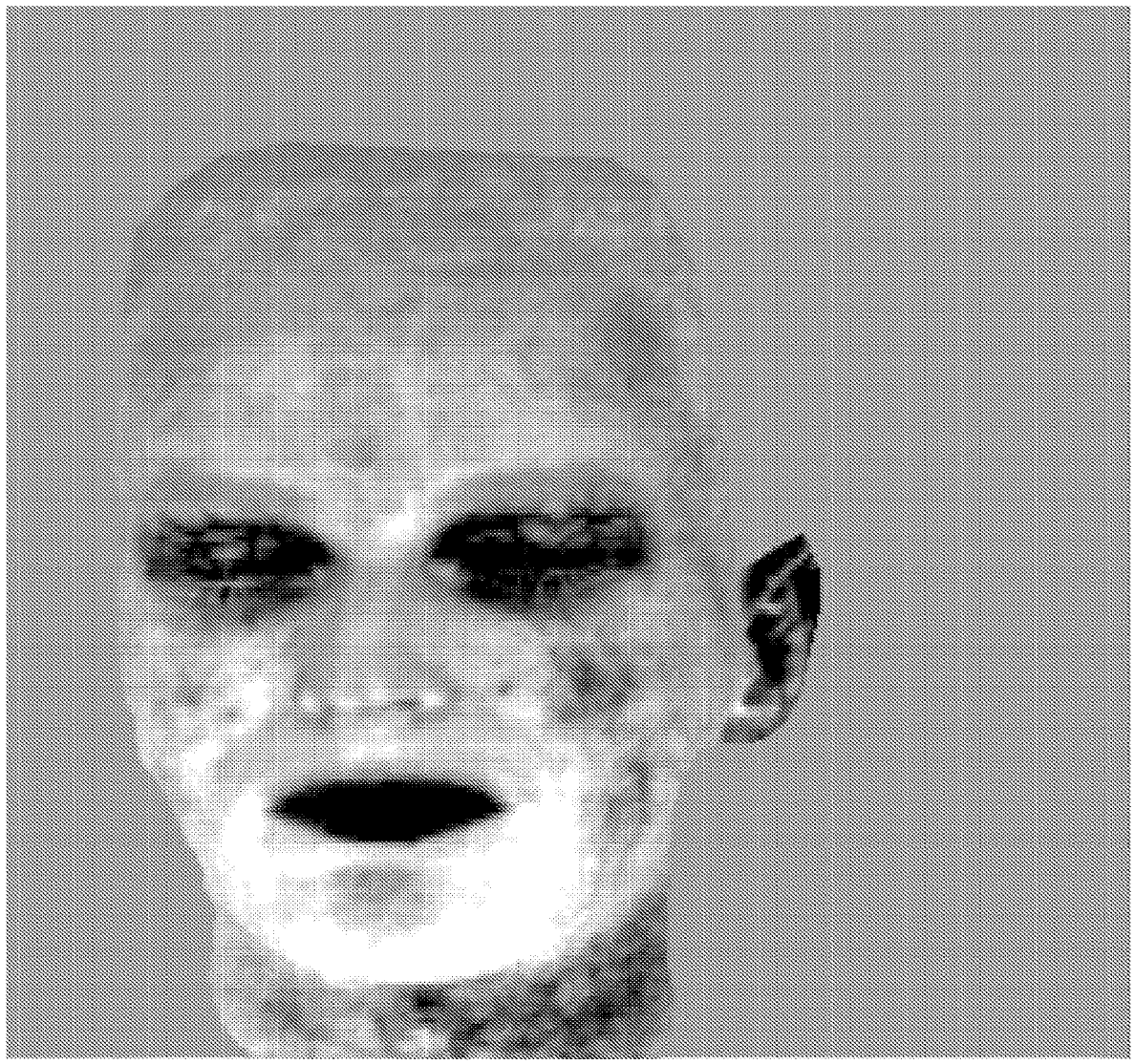
Figure 7C:
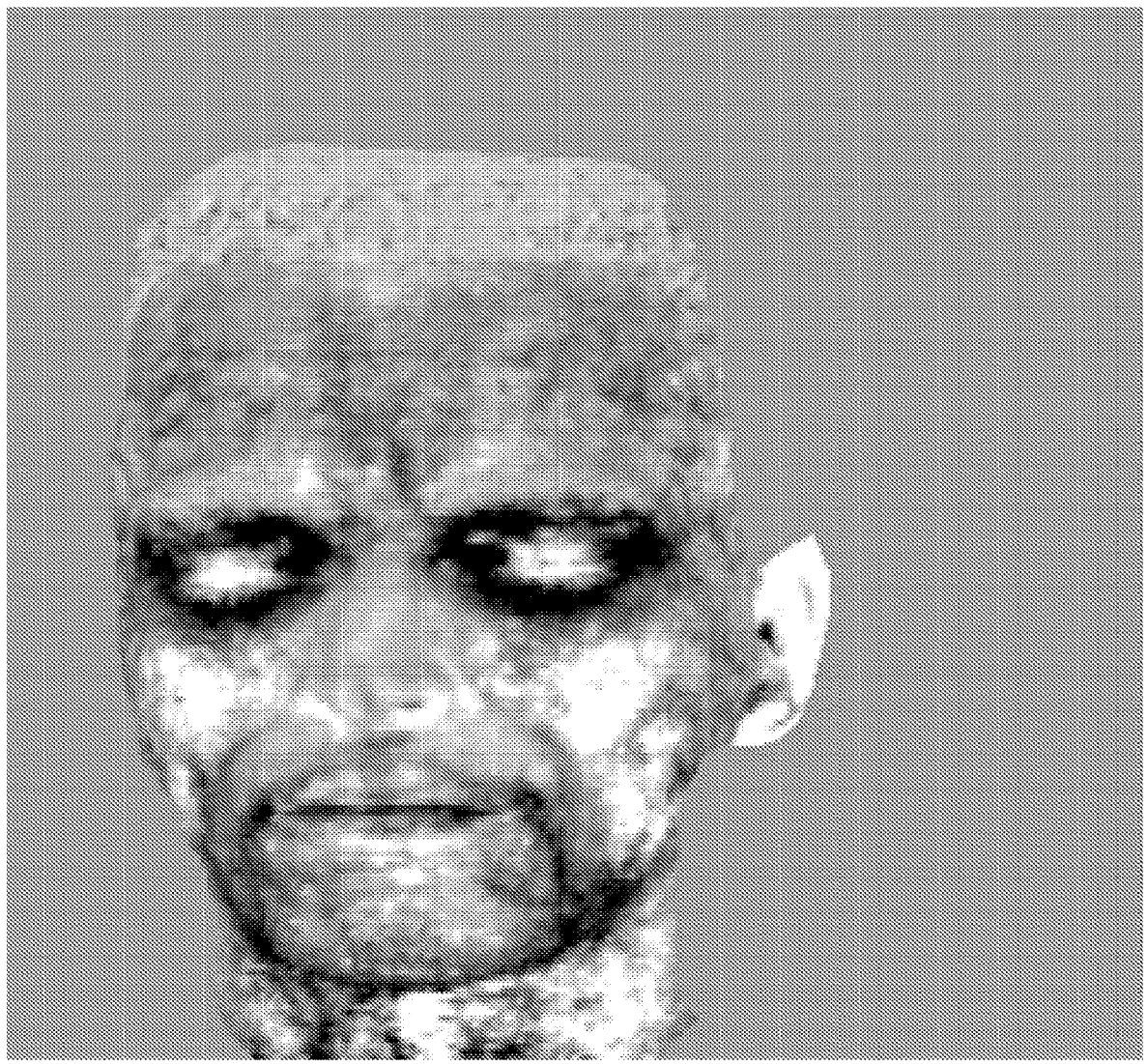

For example, as illustrated in FIGS. 7A-7C, different regions of the electromagnetic spectrum contain significantly different information about a subject. FIG. 7A is an image of a subject obtained in the visible portion of the spectrum (e.g., is a conventional video or photographic image of the subject). FIG. 7B is an image of the same subject, but obtained in the thermal portion of the spectrum (e.g., SWIR to MIR). FIG. 7C is another image of the same subject but obtained in still another portion of the spectrum. The different images were obtained with appropriate conventional sensors that are known in the art, and highlight different aspects of the medical condition of the subject. By obtaining relevant information in the appropriate electromagnetic band(s), and combining that information with an image representing spectral information about the subject such as that described herein, images can be generated that provide significantly more detailed information than an image that represents only a single type of information.

Referring again to FIG. 1, the image, which optionally also contains other information about the subject, is either projected onto the subject (170) or displayed on a video display (180). In embodiments in which the image is projected onto the subject (170), the regions of the image corresponding to regions of the subject are projected directly, or approximately directly, onto those regions of the subject. This allows a physician to concurrently or contemporaneously inspect the physical regions of the subject as well as the image, which is a visible representation of selected spectral features generated by those physical regions. This allows the physician to easily correlate those spectral features with physical features of the subject, thus aiding in the diagnosis and treatment of a medical condition.

Alternately, in embodiments in which the image is displayed on a video display (180), the physician can inspect the image, optionally while he is physically examining the subject, and thus obtain information that is useful in diagnosing and treating a medical condition. A normal (visible light) image of the regions of the subject is displayed underlying the image containing spectral information, which can aid the physician's ability to correlate the spectral features with physical features of the subject. In some embodiments, the image is both projected onto the subject and displayed on a video monitor.

In some embodiments, the image and/or the spectra are stored for later processing. For example, storing an image of a lesion each time the subject is examined can help the physician track the growth of the lesion and/or its response to treatment. Storing the spectra can enable other information to be obtained from the spectra at a later time, for example, if a certain new kind of tumor is identified and the spectra analyzed to see if the subject has the new type of tumor. An image can be generated based on the second analysis.

Figure 2:
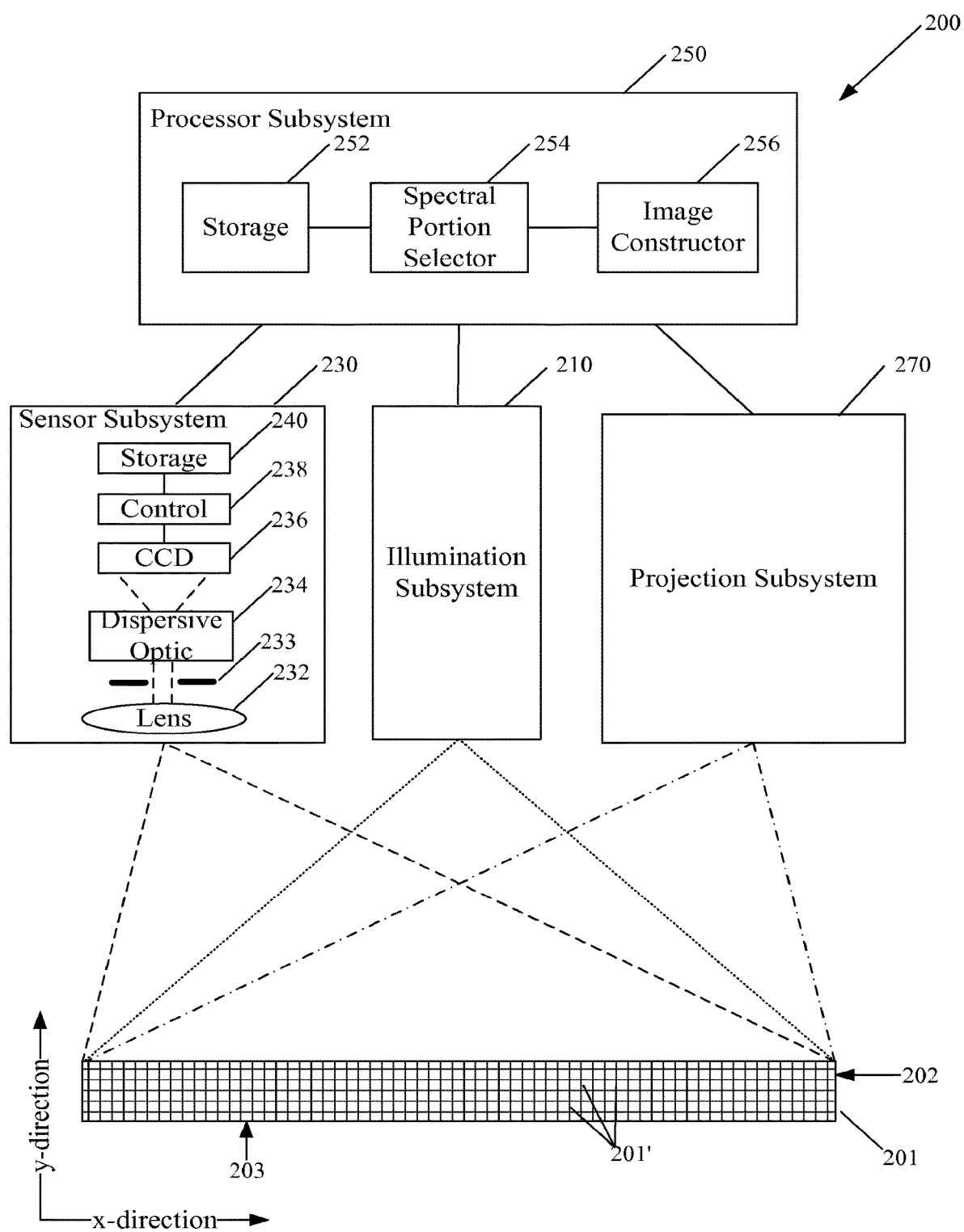
FIG. 2 schematically illustrates a system for hyperspectral medical imaging using real-time projection of spectral information onto a subject, according to some embodiments.

FIG. 2 schematically illustrates a hyperspectral medical imaging system 200 using real-time projection of spectral information onto a subject, according to some embodiments. In FIG. 2, the subject is represented as an area 201 that includes a plurality of regions 201', which are illustrated as a plurality of small squares. The area 201 can be one of the subject's body parts or a portion thereof (e.g., a selected area of the subject's skin), can be multiple body parts or portions thereof, or can even be the entire subject. The plurality of regions 201' are subsets of area 201. The regions 201' need not be directly adjacent one another, and need not be square, or even regularly shaped. The regions 201' collectively represent a sampling of the area 201 that is to be characterized. In the illustrated embodiment, the regions 201' are organized into rows 202 and columns 203 of regions. The subject is, of course, not considered to be part of the imaging system.

The hyperspectral imaging system 200 includes an illumination subsystem 210, a sensor subsystem 230, a processor subsystem 250, and a projection subsystem 270. The processor subsystem 250 is in operable communication with each of the illumination, sensor, and projection subsystems 270, and coordinates the operations of these subsystems in order to irradiate the subject, obtain spectral information from the subject, construct an image based on the spectral information, and project the constructed image onto the subject. Specifically the illumination subsystem 210 irradiates with light each region 201' within area 201 of the subject, which light is represented by the dotted lines. The light interacts with the plurality of regions 201' of the subject. The sensor subsystem 230 collects light from each region of the plurality of regions 201' of the subject, which light is represented by the dashed lines. The sensor subsystem 230 resolves the light from each region 201' into a corresponding spectrum, and generates a digital signal representing the spectra from all the regions 201'. The processor subsystem 250 obtains the digital signal from the sensor subsystem 230, and processes the digital signal to generate an image based on selected portions of the spectra that the digital signal represents. The processor subsystem 250 then passes that image to projection subsystem 270, which projects the image onto the plurality of regions 201' of the subject, the light from which is represented by the dash-dot lines.

Each of the subsystems 210, 230, 250, and 270 will now be described in greater detail.

Illumination Subsystem

Illumination subsystem 210 generates light having a spectrum that includes a plurality of component wavelengths. The spectrum can include component wavelengths in the ultraviolet (UV) band (in the range of about 10 nm to about 400 nm); visible band (in the range of about 400 nm to about 700 nm); near infrared (NIR) band (in the range of about 700 nm to about 2500 nm); mid-wave infrared (MWIR) band (in the range of about 2500 nm to about 10 µm); long-wave infrared (LWIR) band (in the range of about 10 µm to about 100 µm); and/or terahertz (THz) band (in the range of about 100 µm to about 1 mm), among others. The NIR, MWIR, and LWIR are collectively referred to herein as the infrared (IR) band. The light can include a plurality of component wavelengths within one of the bands, e.g., a plurality of wavelengths in the NIR band, or in the THz. Alternately, the light can include one or more component wavelengths in one band, and one or more component wavelengths in a different band, e.g., some wavelengths in the visible, and some wavelengths in the IR. Light with wavelengths in both the visible and NIR bands is referred to herein as "VNIR." Other useful ranges may include the region 1,000-2,500 nm (short-wave infrared, or SWIR).

The illumination subsystem 210 generates the light using one or more light sources. For example, the illumination subsystem 210 can include a single broadband light source, a single narrowband light source, a plurality of narrowband light sources, or a combination of one or more broadband light source and one or more narrowband light source. By "broadband" it is meant light that includes component wavelengths over a substantial portion of at least one band, e.g., over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. By "narrowband" it is meant light that includes components over only a narrow spectral region, e.g., less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source.

One example of a suitable light source for use in illumination subsystem 210 is a diffused lighting source that uses a halogen lamp, such as the Lowel Pro-Light Focus Flood Light. A halogen lamp produces an intense broad-band white light which is a close replication of daylight spectrum. Other light sources that can be used in illumination subsystem 210 include a xenon lamp, a hydrargyrum medium-arc iodide lamp, and/or a light-emitting diode. Other types of light sources are also suitable.

Depending on the particular light source(s) used, illumination subsystem 210 can generate light in which the relative intensities of its component wavelengths are uniform (e.g., are substantially the same across the spectrum), or vary smoothly as a function of wavelength, or are irregular (e.g., in which some wavelengths have significantly higher intensities than slightly longer or shorter wavelengths), and/or can have gaps. Alternatively, the spectrum can include one or more narrow-band spectra in regions of the electromagnetic spectrum that do not overlap with each other.

In some embodiments, illumination subsystem 210 substantially uniformly irradiates regions 201' with light. That is, the intensity of light at one region 201' is substantially the same as the intensity of light at another region 201'. In other embodiments, the intensity of the light varies from one region 201' to the next.

Illumination subsystem 210 is useful because it irradiates regions 201' with light of sufficient intensity to enable sensor subsystem 230 to obtain sufficiently high quality spectra from those regions 201', that is, that a spectrum with a sufficient signal-to-noise ratio can be obtained from each region 201' to be able to obtain medical information about each region 201'. However, in some embodiments, ambient light, such as fluorescent, halogen, or incandescent light in the room, or even sunlight, is a satisfactory source of light. In such embodiments, the illumination subsystem 210 is not activated, or the system may not even include illumination system 210. Sources of ambient light typically do not communicate with the processing subsystem 250, but instead operate independently of system 200.

The light from illumination subsystem 210 (illustrated as dotted lines in FIG. 2) interacts with the plurality of regions 201' within area 201. The interaction between the light and each region 201' depends on the particular physiological structure and characteristics of that region. The particular interactions between the light and each individual irradiated region of the subject impart a spectral signature onto the light obtained from that region. This spectral signature can be used to obtain medical information about the subject. Specifically, different regions interact differently with the light depending on the presence of, for example, a medical condition in the region, the physiological structure of the region, and/or the presence of a chemical in the region. For example, fat, skin, blood, and flesh all interact with various wavelengths of light differently from one another. Similarly, a given type of cancerous lesion interacts with various wavelengths of light differently from normal skin, from non-cancerous lesions, and from other types of cancerous lesions. A given chemical that is present (e.g., in the blood, or on the skin) interacts with various wavelengths of light differently from other types of chemicals. Thus, the light obtained from each irradiated region of the subject has a spectral signature based on the characteristics of the region, which signature contains medical information about that region.

For example, the structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the entire contents of which are hereby incorporated by reference herein.

The dermis has a dense collection of collagen fibers and blood vessels, and its optical properties are very different from that of the epidermis. Absorption of light of a bloodless dermis is negligible. However, blood-borne pigments like oxy- and deoxy-hemoglobin and water are major absorbers of light in the dermis. Scattering by the collagen fibers and absorption due to chromophores in the dermis determine the depth of penetration of light through skin.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see R. R. Anderson and J. A. Parrish, "The optics of human skin," Journal of Investigative Dermatology 77(1), 13-19 (1981), the entire contents of which are hereby incorporated by reference herein. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Using a two-layer optical model of skin, the overall reflectance can be modeled as:

$$R(\lambda) = T_E^2(\lambda) R_D(\lambda),$$

where $T_E(\lambda)$ is the transmittance of epidermis and $R_D(\lambda)$ is the reflectance of dermis. The transmittance due to the epidermis is squared because the light passes through it twice before emerging out of skin. Assuming the absorption of the epidermis is mainly due to the melanin concentration, the transmittance of the epidermis can be modeled as:

$$T_E(\lambda) = \exp(d_E c_m(\lambda)),$$

where $d_E$ is the depth of the epidermis, $c_m$ is the melanin concentration and $m(\lambda)$ is the absorption coefficient function for melanin. For further details, see S. L. Jacques, "Skin optics," Oregon Medical Laser Center News Etc. (1988), the entire contents of which are hereby incorporated by reference herein.

The dermis layer can be modeled as a semi-infinite homogeneous medium. The diffuse reflectance from the surface of dermis layer can be modeled as:

$$R_D(\lambda) = \exp\left(\frac{-A}{\sqrt{3\left(1 + \frac{\mu_s(\lambda)}{\mu_a(\lambda)}\right)}}\right),$$

where constant A is approximately 7-8 for most soft tissues, and $\mu_a(\lambda)$ is the overall absorption coefficient function of the dermis layer. For further details, see S. L. Jacques, "Diffuse reflectance from a semi-infinite medium," Oregon Medical Laser News Etc. (1999), the entire contents of which are hereby incorporated by reference herein. The term $\mu_a(\lambda)$ can be approximated as:

$$\mu_a(\lambda) = c_o o(\lambda) + c_h h(\lambda) + c_w w(\lambda),$$

where $c_o$, $c_h$, and $c_w$ are the concentrations of oxy-hemoglobin, deoxy-hemoglobin and water, respectively, while $o(\lambda)$, $h(\lambda)$, and $w(\lambda)$ are the absorption coefficient functions of oxy-hemoglobin, deoxy-hemoglobin, and water, respectively. For further details, see S. Wray et al., "Characterization of the near infrared absorption spectra of cytochrome aa3 and haemoglobin for the non-invasive monitoring of cerebral oxygenation," Biochimica et Biophysica Acta 933 (1), 184-192 (1988), the entire contents of which are hereby incorporated by reference herein. The scattering coefficient function for soft tissue can be modeled as:

$$\mu_s(\lambda) = a\lambda^{-b},$$

where a and b depend on the individual subject and are based, in part, on the size and density of collagen fibers and blood vessels in the subject's dermis layer.

From the above equations, for a fixed depth of epidermis layer, the skin reflectance $R(\lambda)$ can be modeled as a function $f$ of seven parameters:

$$R(\lambda) = f(a, b, c_m, c_o, c_h, c_w, \lambda)$$

where a, b, $c_m$, $c_o$, $c_h$, and $c_w$, are as described above. The skin reflectance $R(\lambda)$ may also depend on other variables not listed here. For example, long wavelengths (e.g., in the MWIR, FIR, or THz bands) may interact weakly with the surface of the skin and interact strongly with fat, flesh, and/or bone underlying the skin, and therefore variables other than those discussed above may be relevant.

The value of the skin's reflectance as a function of wavelength, $R(\lambda)$, can be used to obtain medical information about the skin and its underlying structures. For example, when skin cancers like basal cell carcinoma (BCC), squamous cell carcinoma (SCC), and malignant melanoma (MM) grow in the skin, the molecular structure of the affected skin changes. Malignant melanoma is a cancer that begins in the melanocytes present in the epidermis layer. For further details, see "Melanoma Skin Cancer," American Cancer Society (2005), the entire contents of which are hereby incorporated by reference herein. Most melanoma cells produce melanin that in turn changes the reflectance characteristics as a function of wavelength $R(\lambda)$ of the affected skin. Squamous and basal cells are also present in the epidermis layer. The outermost layer of the epidermis is called the stratum corneum. Below it are layers of squamous cells. The lowest part of the epidermis, the basal layer, is formed by basal cells. Both squamous and basal cell carcinomas produce certain viral proteins that interact with the growth-regulating proteins of normal skin cells. The abnormal cell growth then changes the epidermis optical scattering characteristics and consequently the skin reflectance properties as a function of wavelength $R(\lambda)$. Thus, information about different skin conditions (e.g., normal skin, benign skin lesions and skin cancers) can be obtained by characterizing the reflectance R(λ) from the skin. This can be done, for example, using the sensor subsystem 230 and processor subsystem 250, as described in greater detail below.

Sensor Subsystem

The sensor subsystem 230 obtains light from each region 201' and resolves that light into a corresponding spectrum. In some embodiments, the sensor subsystem 230 includes a lens 232 that collects light from a region 201', an optional slit 233 that selects a portion of the collected light, a dispersive optic 234 that spatially separates the light into a plurality of component wavelengths, a charge-coupled device (CCD) 236 that records an intensity of each component wavelength of the plurality of component wavelengths (e.g., the spectrum of the region 201'), a sensor control subsystem 238, and storage device 240 for storing spectra. Storage device can be volatile (e.g., RAM) or non-volatile (e.g., a hard disk drive).

The lens 232 captures at least a portion of the light from each region of the plurality of regions 201', as represented by the dashed lines. The optional slit 233 selects a portion of the light captured by the lens 232. For example, in an embodiment described more fully below, a slit can be used in combination with a scanning optic to sequentially select lines 202 of regions of the subject.

The light obtained from each region of the plurality of regions 201' is then directed onto dispersive optic 234. The dispersive optic 234 can be, for example, a diffractive optic such as transmission grating (e.g., a phase grating or an amplitude grating) or a reflective grating, or a prism or similar dispersive optic. The dispersive optic 234 spatially separates the different component wavelengths of the obtained light, allowing the intensity of each of the component wavelengths (the spectrum) to be obtained for each region 201'.

The CCD 236 is arranged at a fixed distance from the dispersive optic 234. The distance between the CCD 236 and the dispersive optic 234, together with the size of the sensor elements that make up the CCD 236, determines (in part) the spectral resolution of the sensor subsystem 230. The spectral resolution, which is the width (e.g., full width at half maximum, or FWHM) of the component wavelengths collected by the sensor element, is selected so as to be sufficiently small to capture spectral features of medical conditions of interest. The sensed intensity of component wavelengths depends on many factors, including the light source intensity, the sensor element sensitivity at each particular component wavelength, and the exposure time of the sensor element to the component wavelength. These factors are selected such that the sensor subsystem 230 is capable of sufficiently determining the intensity of component wavelengths that it can distinguish the spectral features of medical conditions of interest.

Under control of the sensor control subsystem 238, the CCD 236 senses and records the intensity of each of the component wavelengths (the spectrum) from each region 201' in the form of a digital signal. In some embodiments, the sensor control subsystem stores the digital signal into storage device 240. The sensor control subsystem 238 may be integrated with the CCD 236, or may be in operable communication with the CCD 236. Collectively, the dispersive optic 234 and CCD 236 form a spectrometer (which can also include other components). Note that the efficiency of a dispersive optic and the sensitivity of a CCD can be wavelength-dependent. Thus, the dispersive optic and CCD can be selected so as to have satisfactory performance at all of the wavelengths of interest to the measurement (e.g., so that together the dispersive optic and CCD allow a sufficient amount of light to be recorded from which a spectrum can be obtained).

The light need not be obtained and/or spectrally resolved concurrently from all regions 201'. For example, the light from each individual region 201' can be obtained separately. Or, for example, the light from a subset of the regions can be obtained concurrently, but at a different time from light from other subsets of the regions. Or, for example, a portion of the light from all the regions can be obtained concurrently, but at a different time from other portions of the light from all the regions (for example, the intensity of a particular wavelength from all regions can be measured concurrently, and then the intensity of a different wavelength from all regions can be measured concurrently). In some embodiments, light is obtained from a single row 202 at a time, or a single column 203 at a time.

One example of a suitable sensor subsystem 230 is the AISA hyperspectral sensor, which is an advanced imaging spectrometer manufactured by Specim (Finland). The AISA sensor measures electromagnetic energy over the visible and NIR spectral bands, specifically from 430 nm to 910 nm. The AISA sensor includes a "push broom" type of sensor, meaning that it scans a single line at a time, and has a spectral resolution of 2.9 nm and a 20 degree field of vision.

Figure 3A:
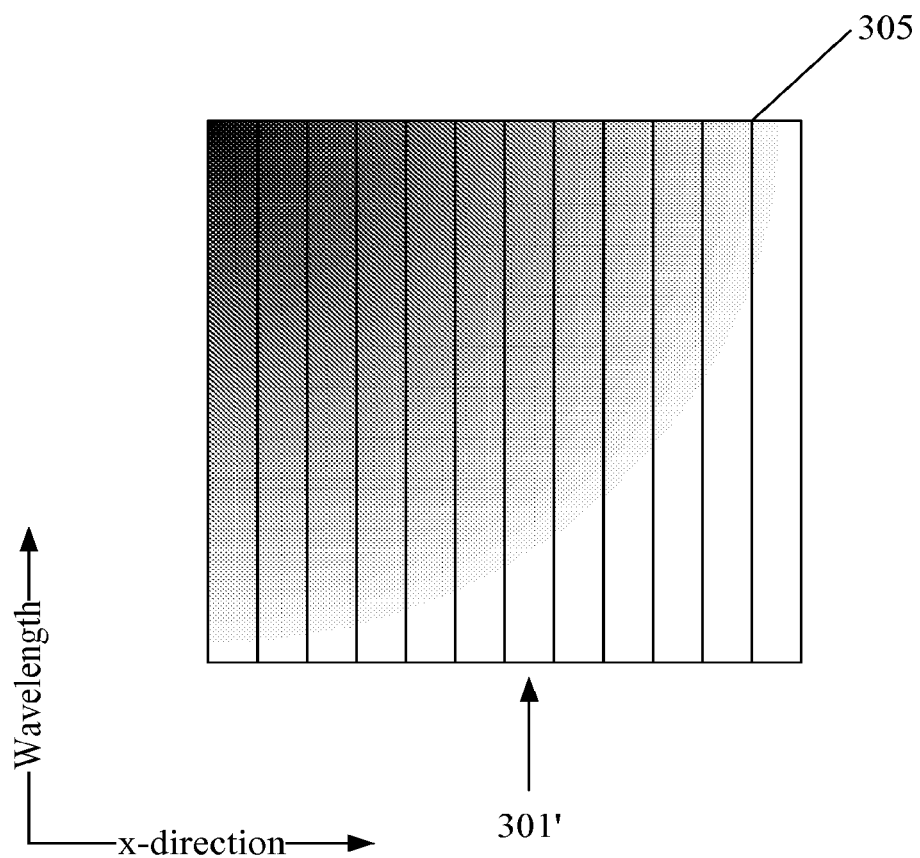
FIG. 3A schematically illustrates a hyperspectral data "plane" including medical information about a subject, according to some embodiments.

During operation, the AISA hyperspectral sensor obtains light from a single row 202 of the regions 201' at a time. The AISA sensor spectrally resolves the light from each of the regions 201' in that row 202 using a dispersive optic. FIG. 3A schematically illustrates the resolution of the spectrum of each region 201' in a row 202 into a "hyperspectral data plane" 305. The plane 305 includes a plurality of columns 301', each of which includes the spectrum of a corresponding region 201'. As FIG. 3A illustrates, the intensity of the spectrum within each column 301' varies as a function of wavelength. This intensity variation is a result of the light's wavelength-dependent interaction with the corresponding region 201' of the subject, and thus contains medical information about that region 201'. For example, using the model described above, the spectrum can be modeled as a wavelength-dependent reflectance R(λ) that is a function of several variables, e.g., the concentrations of melanin, oxy-hemoglobin, deoxy-hemoglobin and water. In the illustrated embodiment, a dark color at a given wavelength means less reflection of light from the region 201' (e.g., strong absorption of that wavelength by the region 201', such as due to a high concentration of melanin) and a light color at a given wavelength means more reflection of light from the region 201' (e.g., weak absorption of that wavelength by the region 201', such as due to a low concentration of melanin). Thus, in FIG. 3, the plane 305 indicates that the left-most columns 301' had a relatively high reflection at long wavelengths, which reflects the fact that the left-most regions 201' of row 202 contain different medical information than the right-most regions 201 of row 202.

After obtaining the plane 305 for row 202, the AISA sensor provides the plane 305 to the processor subsystem 250. The AISA sensor then sequentially obtains additional planes 305 for the other rows 202 within area 201. In some embodiments, the AISA sensor sequentially obtains additional planes 305 by rotating a scanning mirror (not shown) that is mounted in front of lens 232. The scanning mirror directs light from sequential regions of the subject into the sensor for analysis. In other embodiments, the AISA sensor sequentially obtains light from additional regions by moving relative the subject, or by the subject moving relative to the sensor. Other mechanisms can be used to scan sequential regions of the subject, such as the focal plane scanner described in Yang et al., "A CCD Camera-based Hyperspectral Imaging System of Stationary and Airborne Applications," Geocarto International, Vol. 18, No. 2, June 2003, the entire contents of which are incorporated by reference herein.

Figure 3B:
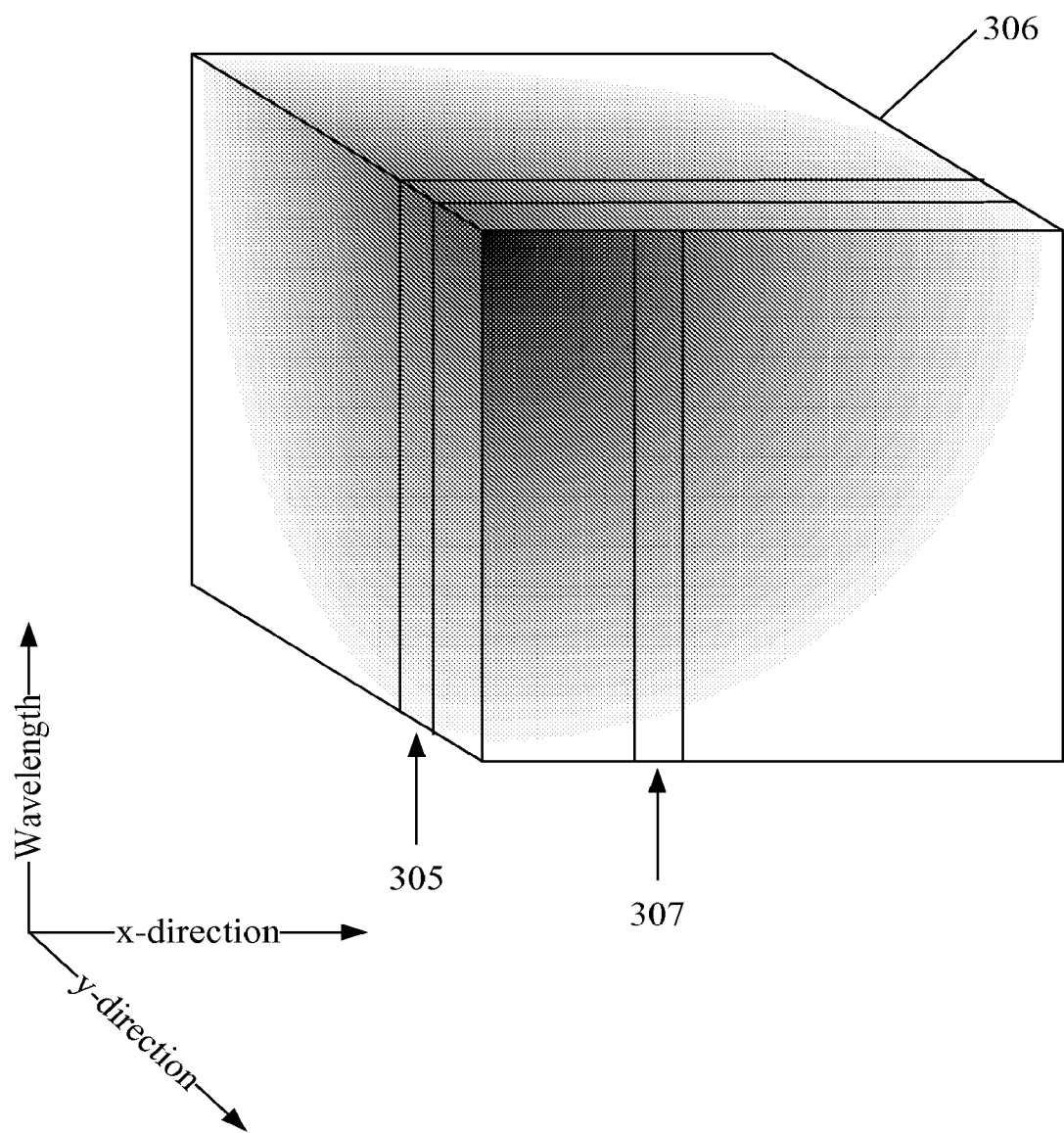
FIG. 3B schematically illustrates a hyperspectral data "cube" including medical information about a subject, according to some embodiments.

FIG. 3B illustrates a "hyperspectral data cube" 306 that the AISA sensor constructs using the planes 305 obtained for each of the rows 202 within area 201. The cube 306 includes a spectrum 307 corresponding to each region 201'. The spectra are stored within a three-dimensional volume, in which two of the axes represent the x- and y-coordinates of the regions 201', and the third axis represents the wavelengths within the corresponding spectra. The intensity at a particular point within the cube 306 represents the intensity of a particular wavelength ($\lambda$) at a particular region 201' having coordinates (x, y). The AISA sensor stores cube 306 in storage device 240. The spectra corresponding to the regions 201' can, of course, be stored in any other suitable format. Sensors other than an AISA sensor can also obtain hyperspectral data planes and cubes.

Other types of sensors are also suitable, such as a liquid crystal tunable filter (LCTF) based hyperspectral sensor. An LCTF-based sensor obtains light from all regions 201' at a time, within a single narrow band at a time. The LCTF-based sensor selects the single band by applying an appropriate voltage to the liquid crystal tunable filter, and recording a map of the reflected intensity of the regions 201' at that band. The LCTF-based sensor then sequentially selects different bands by appropriately adjusting the applied voltage, and recording corresponding maps of the reflected intensity of the regions 201' at those bands. Another suitable type of sensor is a "whisk-broom" sensor that simultaneously collects spectra from both columns and rows of regions 201' in a pre-defined pattern.

Processor Subsystem

Referring again to FIG. 2, the processor subsystem 250 includes a storage device 252, a spectral portion selector 254, and an image constructor 256. The processor subsystem 250 obtains from sensor subsystem 230 a spectrum corresponding to each region 201' of area 201, and stores the spectrum in storage device 252, which can be volatile (e.g., RAM) or non-volatile (e.g., a hard disk drive). Optionally, the spectra are arranged in a hyperspectral data plane or cube, such as those described in greater detail above. Based on information stored in storage device 252, logic operating in the spectral portion selector 250 selects a portion of each spectrum; the selected portion includes medical information about the corresponding region. Then, logic operating in the image constructor 256 constructs an image based on the selected portion of each spectrum. Optionally, the image constructor 256 combines the image with other information about the subject, e.g., images obtained in other electromagnetic bands.

In some embodiments, the spectral portion selector 254 selects the spectral portion based on one or more spectral characteristics of a pre-determined medical condition. For example, as noted above, the reflectance $R(\lambda)$ in the VNIR band of a given region of skin can be modeled as a function $f$ of several parameters. Certain portions of that reflectance $R(\lambda)$ may contain indicia of that medical condition. By selecting spectral portions that potentially include these indicia, the presence or absence of that condition can be determined for the corresponding region.

The spectral portion selector 254 is not limited to selecting spectral regions based on the spectral characteristics of only a single pre-determined condition at a time, but instead can select multiple spectral regions based on multiple pre-determined conditions. For example, as noted above, a physician may not be able to determine through visual inspection whether a lesion is benign or cancerous. Thus it can be useful for the spectral portion selector 254 to select spectral regions based on spectral characteristics of a wide variety of potential conditions.

In one example, a particular medical condition has identifiable spectral characteristics within a narrow, contiguous wavelength range $\lambda_1$-$\lambda_2$ (e.g., 850-900 nm). The spectral portion selector 254 selects the range $\lambda_1$-$\lambda_2$ by applying a filter, e.g., a band-pass filter and/or a band-block filter, to each spectrum. The filter can be digital or analog, and can be smooth (e.g., Gaussian) or can have sharp edges. In embodiments in which a hyperspectral data cube is generated, the spectral portion selector 254 selects portions of the cube that fall within the desired wavelength range. Multiple spectral regions can also be selected, and need not be contiguous with one another. The unused spectral portions need not be discarded, but can be saved in storage 252 for later use. For example, the system may later obtain information from a different portion of the spectrum.

Figure 4A:
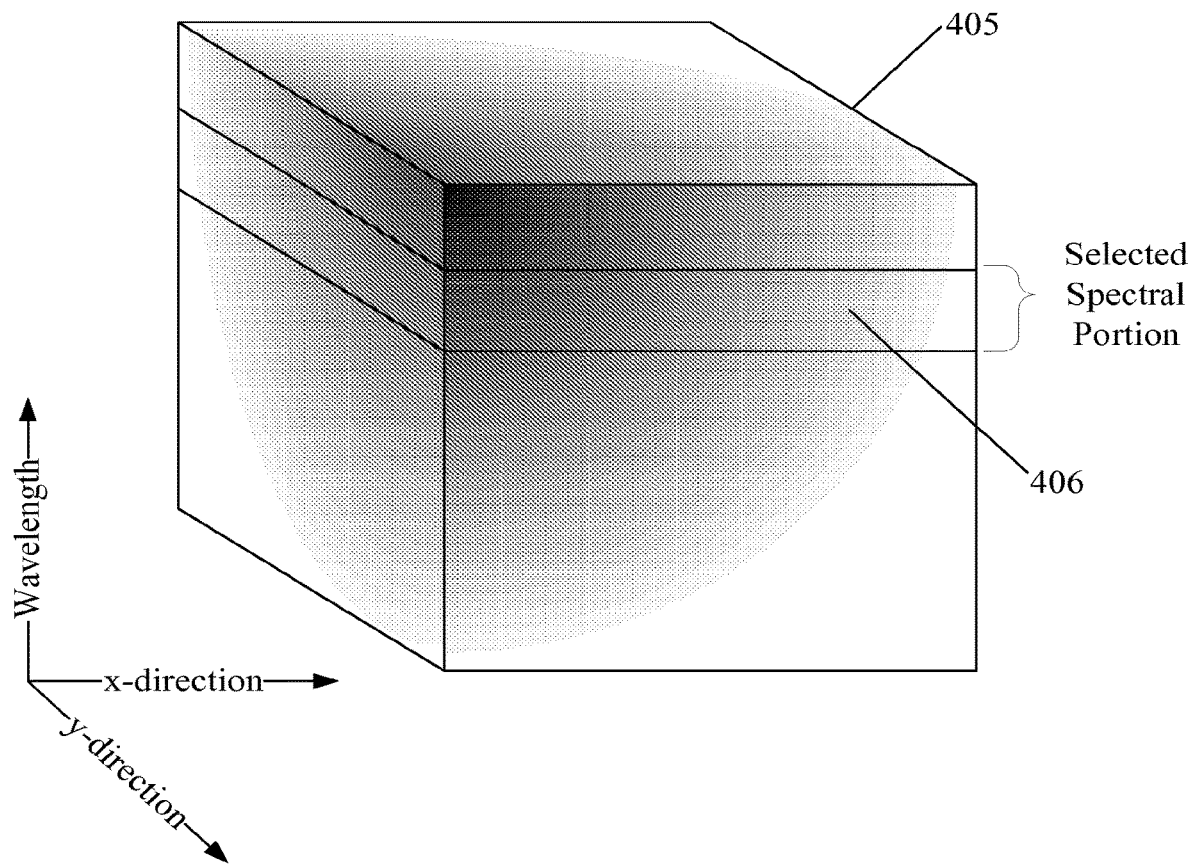
FIG. 4A schematically illustrates selection of a portion of a hyperspectral data "cube" including medical information about a subject, according to some embodiments.
Figure 4B:
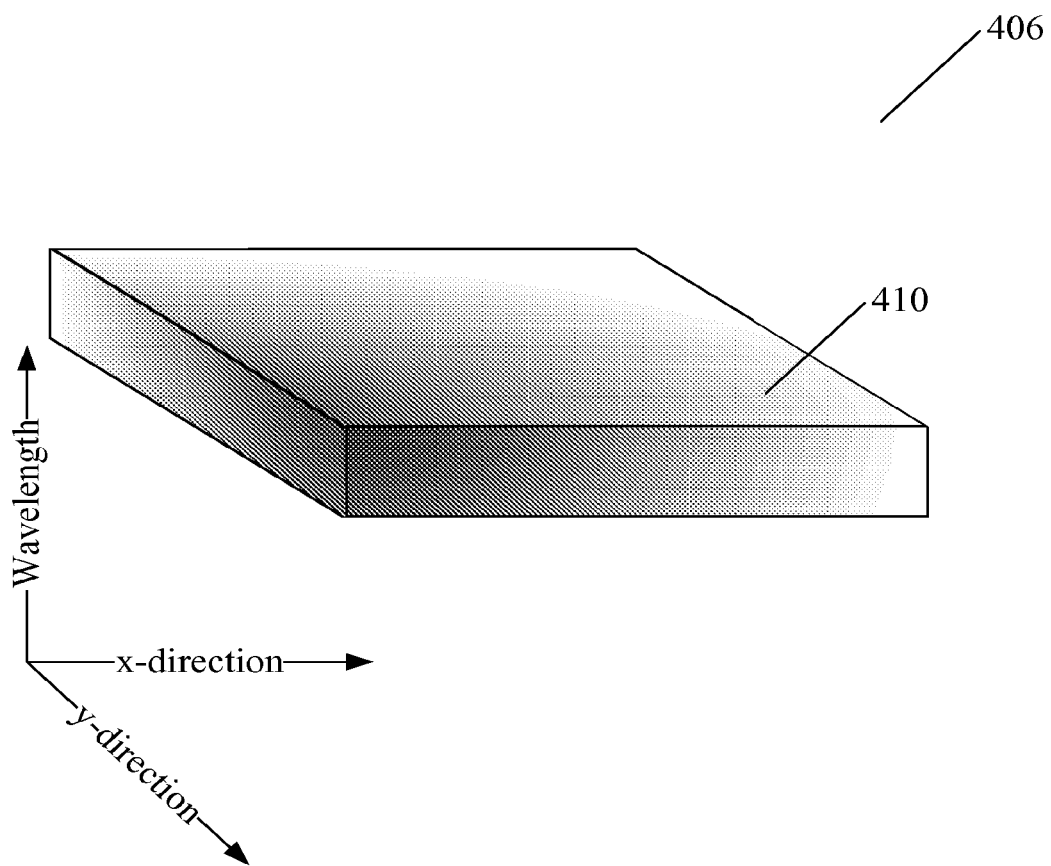
FIG. 4B schematically illustrates a selected portion of a hyperspectral data "cube" including medical information about a subject, according to some embodiments.

FIG. 4A illustrates an embodiment in which the spectra of the different regions 201' are stored in a hyperspectral data cube 405, and the spectral portion selector 254 selects the wavelength region $\lambda_1$-$\lambda_2$ associated with the condition by selecting a volume 406 from the cube 405. The boundaries of volume 406 are defined by the x- and y-dimensions of area 201 and by wavelength range $\lambda_1$-$\lambda_2$. FIG. 4B illustrates a selected volume 406. The intensity distribution at the top face 410 of the volume corresponds to the spectral intensity at wavelength 21 of each region 201' within the area 201, while the intensity distribution at the bottom face (not shown) of the volume corresponds to the spectral intensity at wavelength 22. Thus it can be seen that regions in the lower left corner of the area 201 strongly interacted with light at wavelength $\lambda_1$, while regions in the upper right corner of the area 201 weakly interacted with light at wavelength $\lambda_1$. This indicates that the medical condition is present in the regions in the lower left corner of area 201, but not in the regions in the upper right corner of area 201.

Figure 5:
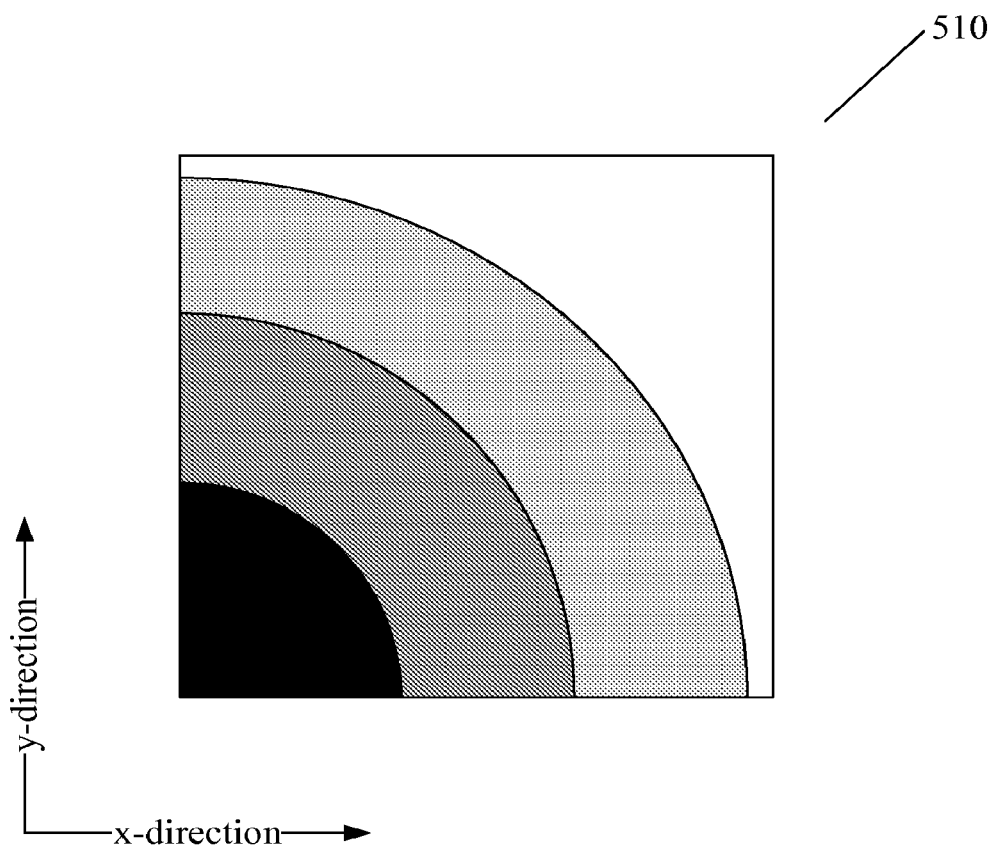
FIG. 5 schematically illustrates an image based on a portion of a spectrum, according to some embodiments.

After the spectral portion selector 254 selects a portion of each spectrum, the image constructor 256 constructs an image based on the selected portion of each spectrum. Specifically, the image constructor 256 creates a representation (e.g., a 2D or 3D representation) of information within the selected portions of the spectra. In one example, the image constructor 256 constructs a two-dimensional intensity map in which the spatially-varying intensity of one or more particular wavelengths (or wavelength ranges) within the selected spectral portions is represented by a corresponding spatially varying intensity of a visible marker. FIG. 5 illustrates an image 510 that is based on the spatial variations in intensity at wavelength 21 that are illustrated in FIG. 4B. The image 510 includes regions 511, 512, and 513 of increasing intensity, respectively, which represent the magnitude of interaction of different regions 201' with light at wavelength $\lambda_1$. While FIG. 5 is monochromatic, false colors can also be assigned to represent different intensities or other information. For example, in embodiments in which multiple spectral portions corresponding to multiple potential conditions are selected, spectral portions corresponding to one condition can be assigned one color, and spectral portions corresponding to another condition can be assigned a different color, thus allowing the physician or other interested part to readily distinguish areas affected by the different conditions.

Figure 6:
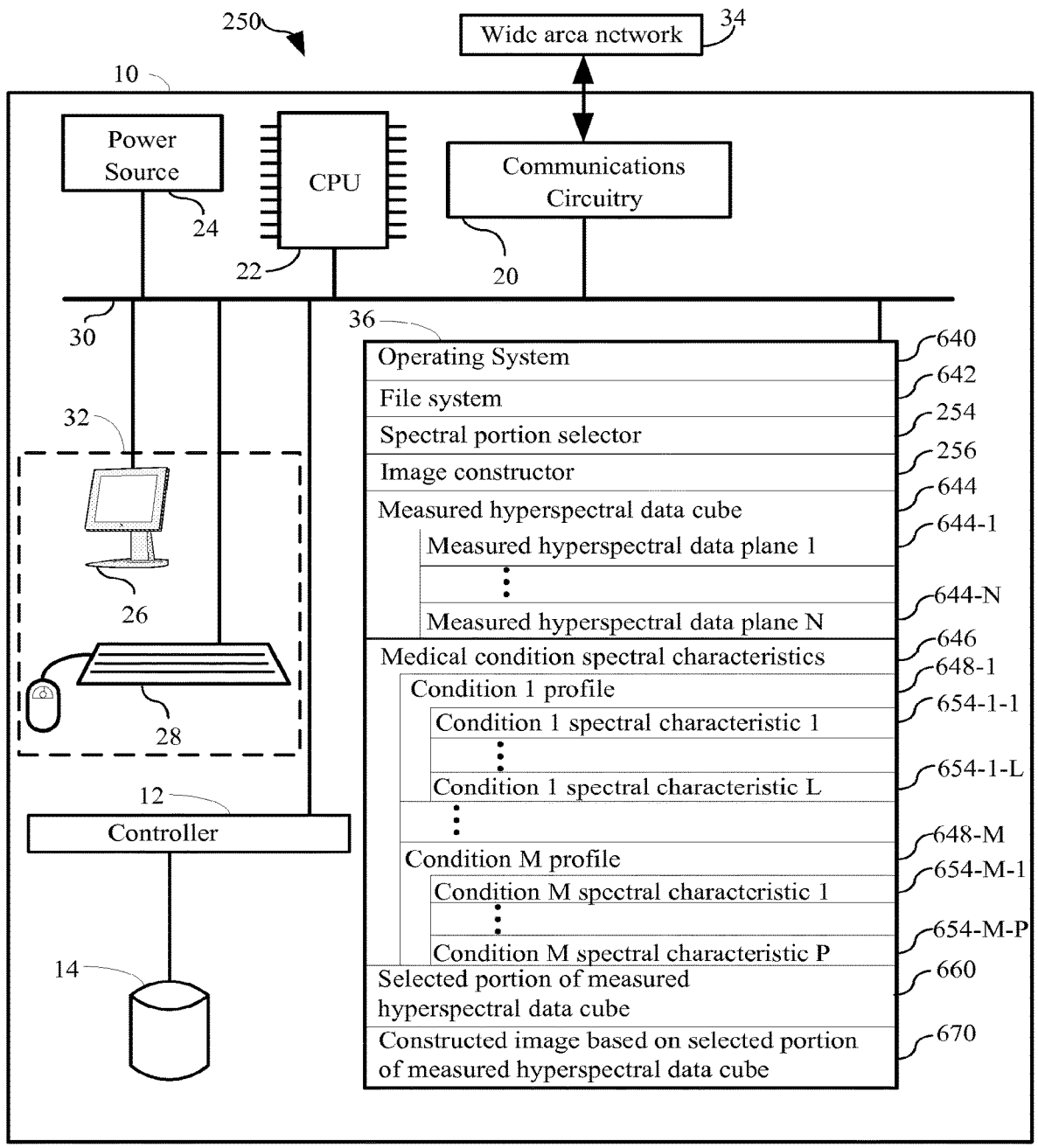
FIG. 6 schematically illustrates an embodiment of a processing subsystem, according to some embodiments.

FIG. 6 schematically illustrates an exemplary embodiment of processor subsystem 250. The subsystem 250 includes a computer system 10 having:

- a central processing unit 22;
- a main non-volatile storage unit 14, for example a hard disk drive, for storing software and data, the storage unit 14 controlled by storage controller 12;
- a system memory 36, preferably high speed random-access memory (RAM), for storing system control programs, data, and application programs, including programs and data loaded from non-volatile storage unit 14; system memory 36 may also include read-only memory (ROM);
- a user interface 32, including one or more input devices (e.g., keyboard 28, a mouse) and a display 26 or other output device;
- a network interface card 20 (communications circuitry) for connecting to any wired or wireless communication network 34 (e.g., a wide area network such as the Internet);
- a power source 24 to power the aforementioned elements; and
- an internal bus 30 for interconnecting the aforementioned elements of the system.

Operation of computer 10 is controlled primarily by operating system 640, which is executed by central processing unit 22. Operating system 640 can be stored in system memory 36. In some embodiments, system memory 36 also includes:

- a file system 642 for controlling access to the various files and data structures used herein;
- the spectral portion selector 254 described above;
- the image constructor 256 described above;
- the measured hyperspectral cube 644, which includes a plurality of measured hyperspectral data planes;
- medical condition spectral characteristics 646 (more below);
- the selected portion of the measured hyperspectral data cube 660; and
- the constructed image based on the selected portion of the measured hyperspectral data cube 670.

The measured hyperspectral data cube 644, the portion selected thereof 660, and the constructed image based thereon 670 need not all be concurrently present, depending on which stages of the analysis that processor subsystem 250 has performed.

As illustrated in FIG. 6, computer 10 includes medical condition spectral characteristics 646, which includes spectral information 648 for a plurality of medical conditions, "Condition 1" through "Condition M." The spectral information for each condition includes a set of spectral characteristics 654 that the spectral portion selector 254 can use to determine whether the region corresponding to the measured hyperspectral data cube 644 has condition 1. In some embodiments, the spectral characteristics 646 are stored in a single database. In other embodiments, such data is instead stored in a plurality of databases that may or may not all be hosted by the same computer 10. In such embodiments, some of the data illustrated in FIG. 6 as being stored in memory 36 is stored on computer systems that are not illustrated by FIG. 6 but that are addressable by wide area network 34.

In some embodiments, the data illustrated in memory 36 of computer 10 is on a single computer (e.g., computer 10) and in other embodiments the data illustrated in memory 36 of computer 10 is hosted by several computers (not shown). In fact, all possible arrangements of storing the data illustrated in memory 36 of computer 10 on one or more computers can be used so long as these components are addressable with respect to each other across computer network 34 or by other electronic means. Thus, a broad array of computer systems can be used.

Projection Subsystem

The projection subsystem 270 obtains the constructed image from the image constructor 256 (which optionally includes other information about the subject, such as images obtained in one or more other electromagnetic bands), and projects the image onto the subject. Preferably, the image is projected such that representations of spectral features are projected directly onto, or approximately onto, the conditions or physiological structures that generated those spectral features. Examples of useful projection systems include liquid crystal display (LCD) projectors and digital signal processing (DSP) projectors.

In some embodiments, some or all of the light forming the image that projection subsystem 270 projects is in a band that overlaps with light in a band that the sensor subsystem 230 obtains. In order to inhibit unwanted feedback of the image light into the sensor subsystem 230, a timer can be used that synchronizes the projection subsystem 270 with the sensor subsystem 230, so that the projection subsystem 270 does not project an image while the sensor subsystem 230 is obtaining light from the subject. In some embodiments, the light forming the image that projection subsystem 270 projects does not spectrally overlap with the light that the sensor subsystem 230 obtains.

As mentioned above, although projection of an image onto the subject can be useful, the image can alternately be displayed on a video display, along with a normal (visible light) image of the subject. In such embodiments the video display would replace the projection subsystem 270 illustrated in FIG. 2. Or, the system could include both the video display and the projection subsystem 270, allowing both modes of viewing information about the subject. The system can include a conventional camera for obtaining a normal (visible light) image of the area 210 of the subject, as well as other subsystems for obtaining different types of information about the subject, which can optionally be included in the projected and/or displayed image.

Medical Conditions

The systems and methods described herein can be used to determine whether the subject has a wide variety of medical conditions. Some examples include, but are not limited to: abrasion, alopecia, atrophy, av malformation, battle sign, bullae, burrow, basal cell carcinoma, burn, candidal diaper dermatitis, cat-scratch disease, contact dermatitis, cutaneous larva migrans, cutis marmorata, dermatoma, ecchymosis, ephelides, erythema infectiosum, erythema multiforme, eschar, excoriation, fifth disease, folliculitis, graft vs. host disease, guttate, guttate psoriasis, hand, foot and mouth disease, Henoch-Schonlein purpura, herpes simplex, hives, id reaction, impetigo, insect bite, juvenile rheumatoid arthritis, Kawasaki disease, keloids, keratosis pilaris, Koebner phenomenon, Langerhans cell histiocytosis, leukemia, lichen striatus, lichenification, livedo reticularis, lymphangitis, measles, meningococcemia, molluscum contagiosum, neurofibromatosis, nevus, poison ivy dermatitis, psoriasis, scabies, scarlet fever, scar, seborrheic dermatitis, serum sickness, Shagreen plaque, Stevens-Johnson syndrome, strawberry tongue, swimmers' itch, telangiectasia, tinea capitis, tinea corporis, tuberous sclerosis, urticaria, varicella, varicella zoster, wheal, xanthoma, zosteriform, basal cell carcinoma, squamous cell carcinoma, malignant melanoma, dermatofibrosarcoma protuberans, Merkel cell carcinoma, and Kaposi's sarcoma.

Other examples include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Some embodiments include differentiating different types of tissue from each other, for example, differentiating bone from flesh, skin, and/or vasculature. Some embodiments exclude the characterization of vasculature.

The levels of certain chemicals in the body, which may or may not be naturally occurring in the body, can also be characterized. For example, chemicals reflective of blood flow, including oxyhemoglobin and deoxyhemoglobin, myoglobin, and deoxymyoglobin, cytochrome, pH, glucose, calcium, and any compounds that the subject may have ingested, such as illegal drugs, pharmaceutical compounds, or alcohol.

OTHER EMBODIMENTS

Some embodiments include a distance sensor (not shown) that facilitates positioning the subject at an appropriate distance from the sensor and/or projector. For example, the system 200 can include a laser range finder that provides a visible and/or audible signal such as a light and/or a beep or alarm, if the distance between the system and the subject is not suitable for obtaining light from and/or projecting light onto the subject. Alternately, the laser range finder may provide a visible and/or audible signal if the distance between the system and the subject is suitable.

The illumination subsystem 210, sensor subsystem 230, processor subsystem 250, and projection subsystem 270 can be co-located (e.g., all enclosed in a common housing). Alternatively, a first subset of the subsystems can be co-located, while a second subset of the subsystems are located separately from the first subset, but in operable communication with the first subset. For example, the illumination, sensing, and projection subsystems 210, 230, 270 can be co-located within a common housing, and the processing subsystem 250 located separately from that housing and in operable communication with the illumination, sensing, and projection subsystems. Alternatively, each of the subsystems can be located separately from the other subsystems. The storage 240 and storage 252 can be in the same device or in two separate devices, and that processor 238 of the sensor subsystem may perform some or all of the functions of the spectral portion selector 245 and/or the image constructor 256 of the processor subsystem 250.

Although illumination subsystem 210 is illustrated as irradiating an area 201 that is of identical size to the area from which sensor subsystem 230 obtains light and upon which projection subsystem 270 projects the image, the areas need not be of identical size. For example, illumination subsystem 210 can irradiate an area that is substantially larger than the region from which sensor subsystem 230 obtains light and/or upon which projection subsystem 270 projects the image. Also, the light from projection subsystem 270 may irradiate a larger area than sensor subsystem 230 senses, for example in order to provide an additional area in which the subsystem 270 projects notations and/or legends that facilitate the inspection of the projected image. Alternately, the light from projection subsystem 270 may irradiate a smaller area than sensor subsystem 230 senses.

Although illumination subsystem 210, sensor subsystem 230, and projection subsystem 270 are illustrated as being laterally offset from one another, resulting in the subject being irradiated with light coming from a different direction than the direction from which the sensor subsystem 230 obtains light, and a different direction than the direction from which the projection subsystem 270 projects the image onto the subject. As will be apparent to those skilled in the art, the system can be arranged in a variety of different manners that will allow the light to/from some or all of the components to be collinear, e.g., through the use of dichroic mirrors, polarizers, and/or beamsplitters. Alternatively, multiple functionalities can be performed by a single device. For example, the projection subsystem 270 could also be used as the irradiation subsystem 210, with timers used in order to irradiate the subject and project the image onto the subject at slightly offset times.

In some embodiments, the spectral portion selector 254 has access to spectral information (e.g., characteristic wavelength bands and/or normalized reflectances $R_N(\lambda)$) associated with a wide variety of medical conditions, physiological characteristics, and/or chemicals. This information can be stored, for example, in storage 252, or can be accessed via the Internet (interface not shown). In some embodiments, the spectral portion selector has access to spectral information for a narrow subset of medical conditions, physiological features, or chemicals, that is, the system 200 is constructed to address only a particular kind of condition, feature, or chemical.

Any of the methods disclosed herein can be implemented as a computer program product that includes a computer program mechanism embedded in a computer-readable storage medium wherein the computer program mechanism comprises computer executable instructions for performing such embodiments. Any portion (e.g., one or more steps) of any of the methods disclosed herein can be implemented as a computer program product that includes a computer program mechanism embedded in a computer-readable storage medium wherein the computer program mechanism comprises computer executable instructions for performing such portion of any such method. All or any portion of the steps of any of the methods disclosed herein can be implemented using one or more suitably programmed computers or other forms of apparatus. Examples of apparatus include but are not limited to the devices depicted in FIGS. 2 and 6.

Further still, any of the methods disclosed herein can be implemented in one or more computer program products. Some embodiments disclosed herein provide a computer program product that comprises executable instructions for performing one or more steps of any or all of the methods disclosed herein. Such methods can be stored on a CD-ROM, DVD, ZIP drive, hard disk, flash memory card, USB key, magnetic disk storage product, or any other physical (tangible) computer readable media that is conventional in the art. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

Some embodiments provide a computer program product that contains any or all of the program modules shown in FIG. 6. These program modules can be stored on a CD-ROM, DVD, magnetic disk storage product, or any other physical computer-readable data or physical program storage product or any other physical (tangible) computer readable media that is conventional in the art. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices.

All references cited herein are hereby incorporated by reference herein in their entirety and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments described herein are offered by way of example only, and the application is to be limited only by the terms of the appended claims, along with the full scope of equivalents to which the claims are entitled.

What is claimed:

1. A method of displaying medical information about a subject, the subject having a plurality of regions of skin, the method comprising:
   resolving light obtained from each region of the skin in the plurality of regions of the skin into a corresponding spectrum;
   selecting portions of each spectrum, the selected portions including medical information about the corresponding region of the skin;
   constructing a spectral image based on the selected portions of each spectrum;
   obtaining other medical information about the subject at the plurality of regions of the skin from a data set, wherein the data set is selected from the group consisting of a thermal image of the plurality of regions of the skin, an x-ray image of the plurality of regions of the skin, a molecular resonance image of the plurality of regions of the skin, a nuclear magnetic resonance image of the plurality of regions of the skin, and a dynamic biomechanical measurement of the plurality of regions of the skin;
   combining the spectral image with the other medical information about the subject to form a composite image; and
   displaying the composite image.

2. The method of claim 1, wherein the displaying the composite image comprises projecting the composite image onto the subject or on a video display.

3. The method of claim 1, wherein the selecting the portions of each spectrum is based on at least one of: a spectral characteristic of a predetermined medical condition, a spectral characteristic of a predetermined physiological feature, and a spectral characteristic of a predetermined chemical.

4. The method of claim 1, wherein the light includes at least one of an ultraviolet wavelength, a visible wavelength, an infrared wavelength, and a terahertz wavelength.

5. The method of claim 1, wherein the combining the spectral image with the other medical information about the subject to form the composite image comprises:
   converting any one of the spectral image and the data set to a topographical or contour map; and
   coloring the topographical or contour map based on the other of the spectral image and the data set, thereby forming the composite image.

6. The method of claim 1, wherein the combining the spectral image with the other medical information about the subject to form the composite image is performed using a data fusion method selected from the group consisting of band overlay, high-pass filtering, intensity-hue saturation transformation, discrete wavelet transform, and principal component analysis.

7. The method of claim 1, wherein the data set is obtained by an independent source selected from the group consisting of x-ray imaging, molecular resonance imaging, nuclear magnetic resonance imaging, and dynamic biomechanical skin measurement probe.

8. The method of claim 7, wherein the spectral image and the data set are obtained substantially concurrently, or sequentially.

9. A system for displaying medical information about a subject, the subject having a plurality of regions of skin, the system comprising:
   a spectrometer for resolving light obtained from each region of the skin in the plurality of regions of the skin into a corresponding spectrum;
   a non-transitory computer-readable medium storing one or more computer programs executable by a computer for:
      selecting portions of each spectrum, the selected portions including medical information about the corresponding region of the skin;
      constructing a spectral image based on the selected portions of each spectrum;
      obtaining other medical information about the subject at the plurality of regions of the skin from a data set, wherein the data set is selected from the group consisting of a thermal image of the plurality of regions of the skin, an x-ray image of the plurality of regions of the skin, a molecular resonance image of the plurality of regions of the skin, a nuclear magnetic resonance image of the plurality of regions of the skin, and a dynamic biomechanical measurement of the plurality of regions of the skin; and
      combining the spectral image with the other medical information about the subject to form a composite image; and
   a display for displaying the composite image.

10. The system of claim 9, wherein the display comprises a projector for projecting the composite image onto the subject or on a video display.

11. The system of claim 9, wherein the selecting the portions of each spectrum is based on at least one of: a spectral characteristic of a predetermined medical condition, a spectral characteristic of a predetermined physiological feature, and a spectral characteristic of a predetermined chemical.

12. The system of claim 9, further comprising a light source for irradiating the subject with the light.

13. The system of claim 12, wherein the light includes at least one of an ultraviolet wavelength, a visible wavelength, an infrared wavelength, and a terahertz wavelength.

14. The system of claim 9, wherein the combining the spectral image with the other medical information about the subject to form the composite image comprises:
   converting any one of the spectral image and the data set to a topographical or contour map; and
   coloring the topographical or contour map based on the other of the spectral image and the data set, thereby forming the composite image.

15. The system of claim 9, wherein the combining the spectral image with the other medical information about the subject to form the composite image is performed using a data fusion method selected from the group consisting of band overlay, high-pass filtering, intensity-hue saturation transformation, discrete wavelet transform, and principal component analysis.

16. The system of claim 9, wherein the data set is obtained by an independent source selected from the group consisting of x-ray imaging, molecular resonance imaging, nuclear magnetic resonance imaging, and dynamic biomechanical skin measurement probe.

17. The system of claim 16, wherein the spectral image and the data set are obtained substantially concurrently, or sequentially.

18. A computer-readable medium storing one or more computer programs executable by a computer for displaying medical information about a subject, the subject having a plurality of regions of skin, the one or more computer programs collectively encoding computer executable instructions for performing the method comprising:
 resolving light obtained from each region of the skin in the plurality of regions of the skin into a corresponding spectrum;
 selecting portions of each spectrum, the selected portions including medical information about the corresponding region of the skin;
 constructing a spectral image based on the selected portions of each spectrum;
 obtaining other medical information about the subject at the plurality of regions of the skin from a data set, wherein the data set is selected from the group consisting of a thermal image of the plurality of regions of the skin, an x-ray image of the plurality of regions of the skin, a molecular resonance image of the plurality of regions of the skin, a nuclear magnetic resonance image of the plurality of regions of the skin, and a dynamic biomechanical measurement of the plurality of regions of the skin;
 combining the spectral image with the other medical information about the subject to form a composite image; and
 displaying the composite image.

19. The computer-readable medium of claim 18, wherein the displaying the composite image comprises projecting the composite image onto the subject or on a video display.

20. The computer-readable medium of claim 18, wherein the selecting the portions of each spectrum comprises selecting the portions of each spectrum based on at least one of: a spectral characteristic of a predetermined medical condition, a spectral characteristic of a predetermined physiological feature, and a spectral characteristic of a predetermined chemical.

21. The computer-readable medium of claim 18, wherein the combining the spectral image with the other medical information about the subject to form the composite image comprises:
 converting any one of the spectral image and the data set to a topographical or contour map; and
 coloring the topographical or contour map based on the other of the spectral image and the data set, thereby forming the composite image.

22. The computer-readable medium of claim 18, wherein the combining the spectral image with the other medical information about the subject to form the composite image is performed using a data fusion method selected from the group consisting of band overlay, high-pass filtering, intensity-hue saturation transformation, discrete wavelet transform, and principal component analysis.

23. The computer-readable medium of claim 18, wherein the data set is obtained by an independent source selected from the group consisting of x-ray imaging, molecular resonance imaging, nuclear magnetic resonance imaging, and dynamic biomechanical skin measurement probe.

24. The computer-readable medium of claim 23, wherein the spectral image and the data set are obtained substantially concurrently, or sequentially.

* * * * *